(12) United States Patent
Komatsu et al.

(10) Patent No.: US 12,344,859 B2
(45) Date of Patent: Jul. 1, 2025

(54) METHOD OF INTRODUCING TARGET-SPECIFIC FOREIGN GENE

(71) Applicant: Chugai Seiyaku Kabushiki Kaisha, Tokyo (JP)

(72) Inventors: Shodai Komatsu, Tokyo (JP); Kenta Komura, Tokyo (JP); Yuuji Wakahara, Tokyo (JP)

(73) Assignee: CHUGAI SEIYAKU KABUSHIKI KAISHA, Tokyo (JP)

( * ) Notice: Subject to any disclaimer, the term of this patent is extended or adjusted under 35 U.S.C. 154(b) by 743 days.

(21) Appl. No.: 17/600,319

(22) PCT Filed: Apr. 1, 2020

(86) PCT No.: PCT/JP2020/014980
§ 371 (c)(1),
(2) Date: Sep. 30, 2021

(87) PCT Pub. No.: WO2020/204055
PCT Pub. Date: Oct. 8, 2020

(65) Prior Publication Data
US 2022/0170047 A1    Jun. 2, 2022

(30) Foreign Application Priority Data
Apr. 2, 2019  (JP) .................................. 2019-070329

(51) Int. Cl.
| | | |
|---|---|---|
| *C12N 5/16* | (2006.01) | |
| *C07K 16/00* | (2006.01) | |
| *C12N 15/85* | (2006.01) | |
| *C12N 15/90* | (2006.01) | |
| *C12P 21/02* | (2006.01) | |

(52) U.S. Cl.
CPC .............. *C12N 15/90* (2013.01); *C07K 16/00* (2013.01)

(58) Field of Classification Search
CPC ...... C12N 15/90; C12N 15/907; C12N 15/85; C07K 16/00; C07K 2317/14; C07K 2317/52; C07K 16/2866
See application file for complete search history.

(56) References Cited

U.S. PATENT DOCUMENTS

| 6,800,457 | B2 | 10/2004 | Koduri et al. | |
|---|---|---|---|---|
| 6,900,052 | B1 * | 5/2005 | Ozaki | C07K 16/00 435/254.11 |
| 8,252,557 | B2 * | 8/2012 | Katayama | C07K 16/00 435/71.1 |
| 9,714,410 | B2 * | 7/2017 | Goto | C12N 5/0037 |
| 2012/0258541 | A1 | 10/2012 | Mauro et al. | |
| 2013/0034875 | A1 | 2/2013 | Sonezaki et al. | |
| 2017/0002059 | A1 | 1/2017 | Jostock et al. | |

FOREIGN PATENT DOCUMENTS

| CN | 1618955 | A | 5/2005 |
|---|---|---|---|
| CN | 104818253 | A | 8/2015 |
| EP | 3176263 | A1 | 6/2017 |
| JP | 2002526071 | A | 8/2002 |
| JP | 2007325571 | A | 12/2007 |
| JP | 4480893 | B2 | 6/2010 |
| JP | 4997253 | B2 | 8/2012 |
| JP | 2015519914 | A | 7/2015 |
| JP | 6053923 | B2 | 12/2016 |
| JP | 2017535258 | A | 11/2017 |
| JP | 6668340 | B2 | 3/2020 |
| WO | WO0017337 | A1 | 3/2000 |
| WO | WO2008151219 | A1 | 12/2008 |
| WO | WO2013190032 | A1 | 12/2013 |
| WO | WO2014205192 | A2 | 12/2014 |
| WO | WO2016064999 | A1 | 4/2016 |
| WO | WO2017184831 | A1 | 10/2017 |
| WO | WO2017184832 | A1 | 10/2017 |
| WO | WO2018118901 | A1 | 6/2018 |
| WO | WO2019030373 | A1 | 2/2019 |

OTHER PUBLICATIONS

Kito et al. (Appl Microbiol Biotechnol, 2002, 60:442-448) (Year: 2002).*
Xu et al. (Plos One, 2015, 10:e0140594) (Year: 2015).*
Aldrich, T. L., et al., "EASE Vectors for Rapid Stable Expression of Recombinant Antibodies," Biotechnol Prog., 19:1433-1438 (2003).
Baser, B., et al., "A method for specifically targeting two independent genomic integration sites for co-expression of genes in CHO cells," Methods, 95:3-12 (2016).
Baumann, M., et al., "Preselection of recombinant gene integration sites enabling high transcription rates in CHO cells using alternate start codons and recombinase mediated cassette exchange," Biotechnol Bioeng., 114:2616-2627 (2017).
Gaidukov, L., et al., "A multi-landing pad DNA integration platform for mammalian cell engineering," Nucleic Acids Res., 46(8):4072-4086 (2018).
GenBank Accession No. NW_003614838.1, "Cricetulus griseus unplaced genomic scaffold, CriGri_1.0 scaffold6779, whole genome shotgun sequence," dated Dec. 18, 2018.
Inniss, M. C., et al., "A Novel Bxb1 Integrase RMCE System for High Fidelity Site-Specific Integration of mAb Expression Cassette in CHO cells," Biotechnol Bioeng., 114(8):1837-1846 (2017).
Koduri, R. K., et al., "An efficient homologous recombination vector pTV(I) contains a hot spot for increased recombinant protein expression in Chinese hamster ovary cells," Gene, 280:87-95 (2001).
Supplementary European Search Report in European Appl. No. EP10820404 dated Oct. 30, 2013.

(Continued)

*Primary Examiner* — David Steadman
*Assistant Examiner* — Joseph R Spangler
(74) *Attorney, Agent, or Firm* — Nixon & Vanderhye P.C.

(57) ABSTRACT

The present disclosure provides a hotspot useful for transformation of animal cells by TI (Targeted Integration). The hotspot of the present disclosure was found near LOC103164262 in the CHO cell genome. Alternatively, the present disclosure relates to transformed cells into which an exogenous DNA has been introduced into said hotspot, and a method of producing a polypeptide encoded by the DNA by culturing the cells.

12 Claims, 6 Drawing Sheets

Specification includes a Sequence Listing.

(56) References Cited

OTHER PUBLICATIONS

Zhang, L., et al., "Recombinase-Mediated Cassette Exchange (RMCE) for Monoclonal Antibody Expression in the Commercially Relevant CHOK1SV Cell Line," Biotechnol Prog., 31(6):1645-1656 (2015).
Zhao, M., et al., "Rapid development of stable transgene CHO cell lines by CRISPR/Cas9-mediated site-specific integration into C12orf35," Appl Microbiol Biotechnol., 102:6105-6117 (2018).
Amaral, M. M. F., et al., "Chapter Eight—Beyond the Natural Proteome: Nondegenerate Saturation Mutagenesis—Methodologies and Advantages," Methods Enzymol., 585:111-133 (2017).
Cacciatore, J. J., et al., "The isolation of CHO cells with a site conferring a high and reproducible transgene amplification rate," J Biotechnol., 164(2):346-353 (2012).
GenBank Accession, JH001259.1, "Cricetulus griseus cell line CHO-K1 unplaced genomic scaffold scaffold6779, whole genome shotgun sequence," Mar. 14, 2015.
GenBank Accession, NCBI Reference Sequence: NW_003614838.1, "Cricetulus griseus unplaced genomic scaffold, CriGri_1.0 scaffold6779, whole genome shotgun sequence," Jul. 12, 2020.
Hamaker, N. K. and Lee, K. H., "Site-specific integration ushers in a new era of precise CHO cell line engineering," Curr Opin Chem Eng., 22:152-160 (2018).
LOC103164262 coiled-coil domain-containing protein 91 [*Cricetulus griseus* (Chinese hamster)] Gene ID: 103164262, updated on Dec. 19, 2023.
Zhou, H., et al., "Development of Site-specific Integration System to High-level Expression Recombinant Proteins in CHO Cells," Chinese Journal of Biotechnology, 23(4):756-762 (2007), with English abstract.
Zhou, S., et al., "Site-specific integration of light chain and heavy chain genes of antibody into CHO-K1 stable hot spot and detection of antibody and fusion protein expression level," Prep Biochem Biotechnol., 49(4):384-390 (2019).
Bahr, S., et al., "Development of a platform expression system using targeted integration in Chinese Hamster Ovary cells," Cell Culture Engineering XVI, ECI Symposium Series, 120 (2018).
Lattenmayer, C., et al., "Identification of transgene integration loci of different highly expressing recombinant CHO cell lines by FISH," Cytotechnology, 51:171-182 (2006).
Lee, J. S., et al., "Site-specific integration in CHO cells mediated by CRISPR/Cas9 and homology-directed DNA repair pathway," Sci Rep., 5:8572 (2015).
Lee, J. S., et al., Accelerated homology-directed targeted integration of transgenes in Chinese hamster ovary cells via CRISPR/Cas 9 and fluorescent enrichment, Biotechnol Bioeng., 113(11):2518-2523 (2016).
Xu, X., et al., "The genomic sequence of the Chinese hamster ovary (CHO)-K1 cell line," Nat Biotechnol., 29(8):735-741 (2011).

\* cited by examiner

SEQUENCE LISTING

<160> NUMBER OF SEQ ID NOS: 3

<210> SEQ ID NO 1
<211> LENGTH: 5040

```
<212> TYPE: DNA
<213> ORGANISM: Cricetulus griseus
<220> FEATURE:
<221> NAME/KEY: misc_feature
<222> LOCATION: (537)..(614)
<223> OTHER INFORMATION: Exon 3
<220> FEATURE:
<221> NAME/KEY: misc_feature
<222> LOCATION: (3147)..(3189)
<223> OTHER INFORMATION: Exon 2

<400> SEQUENCE: 1
```

| | | | | | |
|---|---|---|---|---|---|
| tgagcatcca | aacaaaccct | ctgaggtaca | gcgtcttacg | acacctttac | atggggacat | 60 |
| gacgtctctc | ccttgctctt | gtgagaagat | gagcactgga | tgtggatgcc | tgggcctctg | 120 |
| cagggagaca | ccaagcccctt | aaggcgtatg | cccgggaatg | gtggagctgg | gcaattatga | 180 |
| cagtggctcc | ttgttcacct | ttctgagaaa | cattcacact | gacctcagga | gtatcaggag | 240 |
| tataagccaa | ggtagatgtg | aacgacatat | gttgtactta | aggctcattc | agagtccctt | 300 |
| atacaaccag | cctccagctg | gcacagaatg | ggaaaaaagg | aaatttggat | tcagactgtt | 360 |
| ctaggtctct | acattttca | gatcaaaaaa | ccaacaaact | taaacaaaaa | aaaaatgaga | 420 |
| actgggtttt | acaaacaaac | aaacaaaatc | actttagata | caggaaagaa | agaatcctgt | 480 |
| aaccaggacg | caatacctgt | aggaaaggtg | gcccagggga | cagcagggga | cattgcttgg | 540 |
| tttccactgt | gttcaccatc | aaaggtctct | gcggcctgta | agacaaggca | agaccatttg | 600 |
| aaaagaccta | agagctgta | ggttttatca | gtagtcatgc | gcctagcccc | acaggcatgc | 660 |
| ttctgcgatg | agccactcac | tcacattctc | tctgaacacc | cacccactg | ccatctacag | 720 |
| tgccagatcc | cagttccag | gtaaatgact | tccttcctta | tcccaacaac | ctcacgtcaa | 780 |
| tgaaatgttt | atttcgtgtg | tctttcattg | taatttaact | catcatattt | gtccatcggt | 840 |
| gtaaaaattc | ccttaacaat | agacttgagc | aaatctttta | tttgaaaagg | tcatttagat | 900 |
| tagcatgaga | tttagggact | aatctgaaag | agcaggtgag | cctgtcttct | tgaacaatct | 960 |
| ggtctctctg | gtaccaaact | gtagagaatt | acaaaagcca | gcattttcag | tgaatgggct | 1020 |
| ctcctgtttg | gtggcagcta | cttaggacaa | ggcttacaga | gagcacaaag | ttttcagtct | 1080 |
| ctcaggtagc | tgttaaagtg | agattagtat | tatgattagt | attagagagt | taaagtgaga | 1140 |
| tcagagatat | aatgtcataa | ttctaattcc | tcttctgcac | tgagttgcca | gacaactcag | 1200 |
| aagccagagg | acatgggctg | cagaggacag | aagatgaggc | tgcactgtcc | acgcgctgtg | 1260 |
| aaagtgagta | tattggactg | aacacaggac | gaagaccttc | tgctcctcca | tagcagaact | 1320 |
| gaagagcaag | aacgcctgct | gaacacagtc | aaaccacatc | aggaaatgag | tgctagcct | 1380 |
| cctgttgaga | ggactgacac | actgaagtga | cactgaattc | agttgtcact | tgtgaaagca | 1440 |
| gctgcggctt | ttctatggct | ctgccatggt | tgagctgcga | aagatgcttt | gtgtgggacc | 1500 |
| cttaaataac | agcttccagg | caccaaggca | acatctggtc | ctcaatatcc | atggaatctt | 1560 |
| aacaaagttt | tgaatgctcc | atttaacacg | aatgagactc | caaacataaa | ctattagata | 1620 |
| aaagcatgga | acactcaaat | gagttttta | aaaagcagtt | tgggatgaaa | catggaatgc | 1680 |
| atgcacatct | acactgacag | cctgcacaca | gaaaacccac | atgtctacac | tggctgccca | 1740 |
| cacacagaaa | acctatatgt | ctatactgga | tgtctgcaca | tggagaacat | gtgtctatag | 1800 |
| catttccctg | cacatgaaga | acatgtctac | acagcatgtg | tgtctatagt | agttgcctgc | 1860 |
| acatggagaa | catgtgtgtc | tatagtagtt | gcctgcacat | ggagaacatg | tgtgtctata | 1920 |
| gtagttgcct | gcacatggac | aacatgtgtg | tctataatac | ttaactgcac | atggacagca | 1980 |

```
tgtgtgtcta tagtggttgc ccgcacatgg agaacatgtg tgtctacagc agttgctgcc    2040
tgtacctgaa gaacacacgt gtgtgcaccg actgcccgca cactggcagc tatgataaca    2100
aatgacctgc tgctgaaaac ggccactgtt ctgccttgaa aatgccccca cttctccatc    2160
gacagtaatt gcacccctaa cttttacagc tctcttttta ccaaatccaa actaggtgaa    2220
caactaaaaa acaagaagaa gaaagttctg agctcacaca gtgggtggtt ccaagtcttg    2280
agccctggca tttgactctt aatccagaga ttttcctgca agactatact ggctccgcaa    2340
aaataactgg tttataaaat attccaataa aacgagcaca cattgaaaag ctcacaatgc    2400
ctgcttacaa atgtcccacc aaaccctgag agagcggtgt ggaactgcag caatgatcat    2460
tgccaccagc tggacgtctg cgtgtgtcac acacaaaaac cacggggggg ggggggggg    2520 gggggggggg ggagggggg ggggggcgc ctgacacgtt ctaacagatg tgtccccatc     2580
ctctagtgac agtctgagct cttcctgatg cctcaccagc cacattaatt accctgattt    2640
aaatccttcc tatggcaaga gcaaagcgtc aataacaacc catccctgag tctctccatt    2700
tcccttgact tcgatctctg tttcagaatt acatcaaagc gactaagaat agaacatgag    2760
ggtaggagca accactcagt cagtaaactg tctgccttgc aagcacagaa ccagagtttc    2820
ttccccaaga cgcactctta acagatctgg gcacggtggc gtgcatttgt aatcccagtg    2880
ctaggaaaga tgatccctga ggcttgctag ccagactgca cagtctactt gacaagctcc    2940
aggccagtga aagaccctgt ccaaaagaaa aatgaacggg accaagtaag agacctaagt    3000
ggttgtcctc tgggatctag acgctcatgc acacggagca gcagcagaca cacactcggt    3060
gaataacaga tcaaggaaac agtgaaagta aacacatttt tgtaatagtt tattgttacc    3120
caaagttaaa aacagatgac acttacctcg aagccaccaa agtcgtcatc gtccatcttc    3180
aagcagcacc tgaaacacag aacaactgag atgagacaag ccacctgcat ccaagcacgc    3240
ctgtgactta aaggaatata cactctgagc tgtaaattaa agctgtttca tttgggttat    3300
gaagggcttt cttaaactgt attgtgcatt ttttatcact taaaaaaaaa cagctagtaa    3360
ttggttattt ttttactttc tggcaaaatt agcaatttct ggaactttt cagtaaccat     3420 gtattttgcc attttctgtt gagactccag gagtggaaaa aatattcttt tacattttaa    3480
tttgcttttc ccaaagtggc gctaggcccc atcagtaatg cttcctgctt tccgaatcta    3540
ctcctcagct gcctggcagc atcagcacaa actccagtta agaacaggac tgtggttgag    3600
tttttggaaa tctgtccccc accacaaagg ttcttccctc ggtttcatgg ccgggctgag    3660
ttagattctc aaagttgatc agcattttg aacggtggcc acgacttctg gagcatttga     3720
tatgtgtatt tttagccgaa actgctttgc acttctggaa aaatgtggag caagttactg    3780
agccgatcaa ggtaaatcaa gtcgtgtgtt cacgagatga ggcagaaaac atgagaggac    3840
ccaggatcct tcacacctca ctctcaaggt gggagagaga gcaccgtacc acacgggctg    3900
tgcctctccc taaacacgtt acgggagggt caagggtcaa tcaagcctta gcgccgaggc    3960
ttcagaacta aagcagcggc tttggctcac agcagaaagg aaggaaaatg cccgaaaaaa    4020
ggctggggag taatcgtcac ctatgctccc taagagtgag aacaggaaaa cagaagtgaa    4080
gcccagcagg cctcgctcca gggagccaga agccatgctc aggtccctga ggaacaccta    4140
ccaacaactc catcaaaaga attccacact ccagaactca acagcaaaca aatacactaa    4200
tcacagacag ctttcatgag gccaaccaga ctcatttca caaaaagtat aaagaatgcg      4260
tgtgacagag agcatgataa ttttataagt ggcgctgagt tgctgaaatt gctaacacag    4320
aaaggacaga ggcggcactg ccacggtttg gtcacagcct cacagtctga tgacatttct    4380
```

```
ccaaaaacgt atttcttttt ataaatttag aaattaaagc tcagctagcc atcggtagga      4440
agcacctaga aaatatgaac cagactgcta agaacaacgc tcggtggcgg gtagtctgaa      4500
atgtcatcac gttattcgcg tctcaactga ggacaactct cctctgatga catccgtcag      4560
gaagaaacta tgggagaaga agatgtgcac cctaaggatt accagggaaa ctgtagacac      4620
caccgctgtc ctttcacgtg gatgccacaa acctccaggg tcaaatgccg tgtattttta      4680
gcatctatga acaccactgc actcggggac tcacttctaa agactggagt ttccagagtt      4740
aatgctcccg tgttttcaca aggcttatcc tgacacggga cgggaaggat gccacggagc      4800
cgacaacaca agcacacaac atgttcgcct gtggtaagga agcagattcc taagttctga      4860
tggagctgtg caaaacagca gagtggtgac cgctgacgct ctaggttcca gcaactccta      4920
cgcaccgagg gagacaagac agagttcctc ttctagatgg gcaaaaaagc agtcacgtat      4980
tttatttaaa agtaaataaa tgtgccctgt atatcttaag atatgatgcc tcagaaatgc      5040

<210> SEQ ID NO 2
<211> LENGTH: 6651
<212> TYPE: DNA
<213> ORGANISM: Cricetulus griseus
<220> FEATURE:
<221> NAME/KEY: misc_feature
<222> LOCATION: (6455)..(6651)
<223> OTHER INFORMATION: Exon 1

<400> SEQUENCE: 2
tgtgttaaag acatagcctt tctgaaaata atttagattc aaaccctatg acagtttcct       60
tttgaaaatt aagagaagaa agaaaacgga tgttttttt tttgctgctg attgtgtgtg      120
tgtattttta gaaacaggat ttcgctatgt agccctgact ggcctggaac ttctatttag      180
accaggctgc cttcaaaatt cagagagacc tgcctgcctc tgcctcctga gtactggaat      240
taaaggtgtg agccaccgtg cttgacctca acagcactgg ttttttttaaa actcagtttt      300 acaggggcca gagaaacagc tcagtcaata aagcatttga cacacaagta tatgaagcac      360
tgtttagatc cccagaattc acataaaaag caggtatata taaaaatcct gtaataccag      420
cacttgggag gcagagagag ggaatcctgg gtcaaaatgg ccagctagac tagtctgcac      480
tgtccagctc tggcttcagc aggaaagcct gcctcaaaaa tcagtgatca aaaatcatgc      540
ccaacattta cgttgggact caaacccctca tacacacatg agcatgcaaa catgcagccc      600
acaaatacac aaacatacaa aaaggtcatt gatttacaac acacaaaagt taaaaagcaa      660
tttttaagaa ggaaacatca gaggttcttc atggactctg tcacttgaat acactcaacc      720
cttggttctt tctaagccat aatgtgttaa gtcgctgtga aacgtgtctg cagtttgtgt      780
tacagccatt agaactgcag ggattccac atgtgtcaa gtaacccta agcagagaat      840 gatgaggctc taactcagag ctatatccca ctaacttggg accaaggcta aaggttttca      900
tagtatctaa gctcaacaat ctcaggaccc cttgcatgta aattaaccta tcctgttgct      960
ttattatgtt aattccctat tctgccatcc tcagtattta aaacactgac agtacttta     1020 aagtccggtt tgagaaaaac agaccagaga gtaaaacatg cacagggaca gcattgcaca     1080
ccctctgcca ccagccactc cacagatgtc agccaaggtc cttgagaggc tgagtggtga     1140
ggaagaaagc tcagatccag ggaaaaagca cacaggtata aacaacagtg aaaactctta     1200
gggagaaaac tgcctagtgt gggaaaataa ttgagggggg atctatggtt gggaatatca     1260
ggggacttct gagacagact gaaggaaatg aacagaaatt ctaaatagaa cttttaaaaa     1320
```

```
aaaaaagtac atttttatcca agtttccact gaaaggtctt ctttaaaatg acccactccc    1380
cccaccaaaa aaagatgtta cattaaaatg cttgtgtgtg ctcctaaata caaacaaggt    1440
ttaaagaaca aacaaggtaa aggagaaaag tgtgaagcat ggcagggaag aacagaggtg    1500
gctcagcccc atttccctca ggctacccac agaaggctca agaatgagca actagcagtt    1560
ggttaaagat gaggctcaaa ttccaaccaa tcagggctgc acctcaatcg ccaaccaaaa    1620
tcataaagcc agtcagttgc agttcttccc ccagcagaac acaggaagca tgaagacaga    1680
gtttttgcac catctcagtc ttcatgattg aaagcaaaac catgccagtg tgtcctggaa    1740
aatagcagca ctgtgtcaca gcgaggcaca tgaaagcatc agtgctcaag cctcctgct     1800
gtgtctacca cgctttccct ttccttcttg gatgagccgg tgcctgctct gtatctacta    1860
ccaatcagag cgagcacggc ttgatttcag ctaccctta ttacacacgt ttgtgtacat     1920
gtatgtcaga ggacagcctg taggacttgt gagtagacgc ctttatccat tgagccatgt    1980
cgctggtcca atctgtcaac tctctgtagt gtaagcatcc tctaaattgg aagctagtgt    2040
ttcactttt taagggagct ttggatggaa ataattcta ttttttaata ataaattttg      2100
gtcttttta atcttttggt tttagatat atacctgcac ttgctacaaa gaaagctaat      2160
aattttagaa atttaaatgt tcaagcaagc tacagcttaa tatttacatg tagtaaaacc    2220
aaagatctag tttccttta aaaaaatatg gaagttctcc acgccccatt tcctttatta    2280
taaagtaact ttttccttca ctaacctgat actttcttat catataacac attcgttgct    2340
gcagaataaa ctttgtacac tgtaaatatg tataaactat tctcattggt taataaagag    2400
ctgactggcc tagagctagg tgggagaggc agactaggag aattctggga agaagggtgg    2460
agtcagaagt gtccccagcc agacagagag ggaacaagac acactcgaga ggtaaatacc    2520
acaagcctca gggcagcaca tagattaata gaaatgggtt catttaagtt ataagagcta    2580
gttaataata agcctgagct atcaactgag catttaaaat taataagact ctctgactgg    2640
ttacttggga gcggcttgca ggacaaaaac ttccaccaac catttatttc ggaacacaca    2700
gacccatgga tatgtgtgcc tatttctagc tgcagaatta ttttgatggc actgacaccc    2760
atacgggacc aagcagtacc atcctaagcc tggtgcattg tagcttatca gtgaagttgt    2820
catttttcctt agtgaacttt tttctgcatc ttttgtcaag tttacacctg atgctctacg    2880
agtctagtgt ctccttttac attacttaac tatgtcttac gcccatcttt ctttggtaag    2940
ctctcattgg taattgtttt acctgtacat tccttcatgt taattttata tgcaaatgat    3000
catttttgtct ccagacagca agtttccttt cctccattac aatcccacta ccccaggttc   3060
tgttcctttt gtcacttgca taggccatgc tcttcactgc tgccctggtg cctggtgcca    3120
tgcgatgggc tgcacttgct gaagataatt tcaaagccat cttctaaccc atgtgtccct    3180
cttaaagtgg acgccagcac tgtcctctct cctgacacta ggcgcatgtg acctccctaa    3240
caaaatggaa gatagccaag cgcccgccat gtgtgggaat gcagtgtcct ctagcgcctg    3300
ccccatatct cttgccttgg gaatacagat gccagatgca gaaagaccac agcggcccac    3360
acagagacca cttggagaaa ttgtgtgtag gtttcccaac tgattgccaa ccactgacat    3420
cagatctcaa gacacaggaa tgaacacaat ttcagatgac tccaggccac ctcccgtgat    3480
agaatcacca cagctgagga agtaaaaggg agagagagac cgaacaccat tttctacagc    3540
caactccctg acctcagaat ccttagtcat gagtgcgttt ataagcatac aaaagaggag    3600
tacagacgac agtcggttgg ttcctaacag gataaaaggg gtctctcctc cctgtaattt    3660
gctaaacatc atcatcagga attcacatgg cctatcgagt gagactgtca cacagttctc    3720
```

```
gtaatcttgt gtcactcggg agtcaggggt catgggatgg tagccgtcct gtcgcagctg    3780
ggatggtagc cgtcctgtcg cagctgggat gaaccacctg gtaatggggc tgctttctct    3840
catctgctaa tatcctgtct gagatggcta gactacactg aaccaggaat cacctctgga    3900 accccteтct cacagtatct tcatctgact tagatatcag gatggagctg ggctctcaga    3960 actgctgga aatagttcct tttcttctgt aattaaaga gatttcatca gaatgaaaaa      4020
atctatttct tacaacttgg tagaaaaaaa tcataacttg cttagcaaat catctaggac    4080
tgttgcttgc tctgtgggaa gattcagttt cttctaatta tgggacaatt cggacttta    4140 attttttccag aagcttctgt aaataatatt ttttctaga aaacctattt ttaaatggtt   4200
ggcatacagt tattaacatt catttcaaat ttaatttgga aacaagcttg ttttacctgt    4260
caatcccagt tccctctccc taccctaaca ttcttcttgt tatcactatt ttaatgtctg    4320
atttatctgc cattcttttc attttatatg tactgagcga tgtgttattt aaatcttcta    4380
catcctatgg gtctctactt tgtttcactt tttatctaat tcaactcagg tgagttgaaa    4440
cctttgccac agtagcagca gagccaacag catctgggtt ctagcaggtt agggaaggga    4500
taaattctag ttttctactg aaaacaaac gactggaagt gattgtaagg tcagatgtgt     4560
gtgcgtcagg gtttagttca gtggttttgg ttctctaaca cactcattca gtctatttta    4620
gaaacaccag tcatctggcg taagaaaagg tatgccattt catgacataa atcatctcaa    4680
gctttaaaaa atagtaatgg gaggggtgga ggatggtctg atggttagcg cactggctgc    4740
tcttgcagag gtccagattc ggttcctagc acccacacgg gggctcacaa ctgcctgtac    4800
ctccagttcc taatgatcta caccctcttc tggcttccac aagcactgca caaacttggt    4860
gcacaaacat gcacacagat aaaactcaca cacacccaca taaacagtaa aaagtaaata    4920
aaataataac aggcataaat tacaagacca acaacaacaa agaaaaaaat gttcaaaatt    4980
acagtgacaa ggcagaacca gcaagtggat actataagga cttagttttt agattttttt    5040
ttttcgtgtg tgtgtgtgtg tgtgtgtgtg tgtgtgtgtg tgtgtgtgtg tgtgtgtgcg    5100
cgcgcgcaca tgttcatgtc acaacaagaa tgtgtaggtc cgtggaaacg ttacaggagc    5160
tggttctctc cttccactat gcaggttcca gggatcaaac ttagcagcaa gcaccaaccc    5220
ccaaaacttt tcaatgtaac caatttaaaa atacaatgga ggcacatgga agcacatgca    5280
cacctgcaga tacacactta tgaacacaca agcacatagt atttgaaaag aaaaaagaaa    5340
agcatccact tgtggactaa tgagcatgat cagaaaaatc acctatgctg tagttaaagt    5400
ccccaaagga gaaggcattg agattgcaat gaagtaaata ttgaaaagaa gatggccaaa    5460
aacatctcag gattgattag caacaaacga caagccaagc aaagagagac aacccagcaa    5520
aataaacact ggatgctctc atcaccccaa tatgacatca ataaaacaca atccaaagaa    5580
cccaaacggc acagcgcgtg ggacctcccc aaacggcaca gcgcgtgggc ctctacttcc    5640
tccacctcca acctccccaa actgggacct ccccaaacag gacccgaggt tcccctctac    5700
ttcctccacc tccaggaaca tctgttattc agtccttgca catttcaaga gtaaaaatgt    5760
taaccatcga atgagggaat aaatggcaca gccagactac cttgggattg actggtttgt    5820
cccaacacct ggacttaaga agtgcactat tagagcaacc aacccagaga actagacctg    5880
aatacaaata taaacactgt acacaaacct cagacataat tacagaactg tcttaccaca    5940
catcccctaa aaaattcaga tggtgcagta gcagacccac atataacagt tttctaaatt    6000
ttgctttcaa atgttgccaa catttttgtcc aatttattg tcaaattaat gtagaaatat    6060
```

```
ttcgcaataa tcctactttt tctttgcatt tcaccatgtt tccttctggc agaaagaaat    6120
acatccagac tgcacatgcc atctttaaat tgattttaca tccactgtac tacaaaatta    6180
agtataaagc ttctaatgac cttacaatgg cactttgaat ggctccatta ctaaccaaat    6240
actccatcaa tatacaaatt tggttttgtg ccaattatta aatatctaag acgtcttcat    6300
gcattggctt tgttttcttc ttttaggtta taaatttaat gtaaactccc agatactgag    6360
aaattaacca aaaaaaaatt tatatatata tatattttta tatatatata tatatatatg    6420
tgaacaaggt tccaaaggag ctaaactcca ttaccttaca acttgtaaat tcttcaaaag    6480
cgttgatgtc cccttggact ttagcagagc tatgagctgg gaacaggaga ggtgggggact   6540 ccccaaccaa gagcacagtg gtcccccagt gacaaacagt cagcacgaaa aacatacaga   6600
caagtaataa tacagagact aagtagctta tatttaaggg tgtgtgtgtg t             6651
```

<210> SEQ ID NO 3
<211> LENGTH: 8305
<212> TYPE: DNA
<213> ORGANISM: Cricetulus griseus

<400> SEQUENCE: 3

```
ctgaaacaca gaacaactga gatgagacaa gccacctgca tccaagcacg cctgtgactt      60
aaaggaatat acactctgag ctgtaaatta aagctgtttc atttgggtta tgaagggctt    120
tcttaaactg tattgtgcat tttttatcac ttaaaaaaaa acagctagta attggttatt    180
tttttacttt ctggcaaaat tagcaatttc tggaactttt tcagtaacca tgtattttgc    240
cattttctgt tgagactcca ggagtggaaa aaatattctt ttacatttta atttgctttt    300
cccaaagtgg cgctaggccc atcagtaat gcttcctgct ttccgaatct actcctcagc    360
tgcctggcag catcagcaca aactccagtt aagaacagga ctgtggttga gtttttggaa    420
atctgtcccc caccacaaag gttcttccct cggtttcatg gccgggctga gttagattct    480
caaagttgat cagcattttt gaacggtggc cacgacttct ggagcatttg atatgtgtat    540
ttttagccga aactgctttg cacttctgga aaaatgtgga gcaagttact gagccgatca    600
aggtaaatca gtcgtgtgt tcacgagatg aggcagaaaa catgagagga cccaggatcc    660
ttcacacctc actctcaagg tgggagagag agcaccgtac cacacgggct gtgcctctcc    720
ctaaacacgt tacgggaggg tcaagggtca atcaagcctt agcgccgagg cttcagaact    780
aaagcagcgg ctttggctca cagcagaaag gaaggaaaat gcccgaaaaa aggctgggga    840
gtaatcgtca cctatgctcc ctaagagtga aacaggaaa acagaagtga agcccagcag     900
gcctcgctcc agggagccag aagccatgct caggtccctg aggaacacct accaacaact    960
ccatcaaaag aattccacac tccagaactc aacagcaaac aaatacacta atcacagaca   1020
gctttcatga ggccaaccag actcattttc acaaaaagta taagaatgc gtgtggacag    1080 aagcatgata atttttataag tggcgctgag ttgctagaat tgctaacaca gaaaggacag   1140
aggcggcact gccacggttt ggtcacagcc tcacagtctg atgacatttc tccaaaaacg   1200
tattcttttt tataaattta gaaattaaag ctcagctagc catcggtagg aagcacctag   1260
aaaatatgaa ccagactgct aagaacaacg ctcggtggcg ggtagtctga aatgtcatca   1320
cgttattcgc gtctcaactg aggacaactc tcctctgatg acatccgtca ggaagaaact   1380
atgggagaag aagatgtgca ccctaaggat taccagggaa actgtagaca ccaccgctgt   1440
cctttcacgt ggatgccaca aacctccagg gtcaaatgcc gtgtattttt agcatctatg   1500
aacaccactg cactcgggga ctcacttcta aagactggag tttccagagt taatgctccc   1560
```

| | | |
|---|---|---|
| gtgttttcac aaggcttatc ctgacacggg acgggaagga tgccacggag ccgacaacac | 1620 |
| aagcacacaa catgttcgcc tgtggtaagg aagcagattc ctaagttctg atggagctgt | 1680 |
| gcaaaacagc agagtggtga ccgctgacgc tctaggttcc agcaactcct acgcaccgag | 1740 |
| ggagacaaga cagagttcct cttctagatg ggcaaaaaag cagtcacgta ttttatttaa | 1800 |
| aagtaaataa atgtgccctg tatatcttaa gatatgatgc ctcagaaatg ctgtgttaaa | 1860 |
| gacatagcct ttctgaaaat aatttagatt caaaccctat gacagtttcc ttttgaaaat | 1920 |
| taagagaaga aagaaaacgg atgttttttt ttttgctgct gattgtgtgt gtgtatttt | 1980 |
| agaaacagga tttcgctatg tagccctgac tggcctggaa cttctattta gaccaggctg | 2040 |
| ccttcaaaat tcagagagac ctgcctgcct ctgcctcctg agtactggaa ttaaaggtgt | 2100 |
| gagccaccgt gcttgacctc aacagcactg gttttttaa aactcagttt tacaggggcc | 2160 |
| agagaaacag ctcagtcaat aaagcatttg acacacaagt atatgaagca ctgtttagat | 2220 |
| ccccagaatt cacataaaaa gcaggtatat ataaaaatcc tgtaatacca gcacttggga | 2280 |
| ggcagagaga gggaatcctg ggtcaaaatg ccagctaga ctagtctgca ctgtccagct | 2340 |
| ctggcttcag caggaaagcc tgcctcaaaa atcagtgatc aaaaatcatg cccaacattt | 2400 |
| acgttgggac tcaaacccct atacacacat gagcatgcaa acatgcagcc cacaaataca | 2460 |
| caaacataca aaaaggtcat tgatttacaa cacacaaaag ttaaaaagca attttttaaga | 2520 |
| aggaaacatc agaggttctt catggactct gtcacttgaa tacactcaac ccttggttct | 2580 |
| ttctaagcca taatgtgtta agtcgctgtg aaacgtgtct gcagtttgtg ttacagccat | 2640 |
| tagaactgca gggattccca ccatgtgtca agtaacacct aagcagagaa tgatgaggct | 2700 |
| ctaactcaga gctatatccc actaacttgg gaccaaggct aaaggttttc atagtatcta | 2760 |
| agctcaacaa tctcaggacc cctgcatgt aaattaacct atcctgttgc tttattatgt | 2820 |
| taattcccta ttctgccatc ctcagtattt aaaacactga cagtactttt aaagtccggt | 2880 |
| ttgagaaaaa cagaccagag agtaaaacat gcacagggac agcattgcac accctctgcc | 2940 |
| accagccact ccacagatgt cagccaaggt ccttgagagg ctgagtggtg aggaagaaag | 3000 |
| ctcagatcca gggaaaaagc acacaggtat aaacaacagt gaaaactctt agggagaaaa | 3060 |
| ctgcctagtg tgggaaaata attgaggggg gatctatggt tgggaatatc aggggacttc | 3120 |
| tgagacagac tgaaggaaat gaacagaaat tctaaataga acttttaaaa aaaaaaagta | 3180 |
| cattttatcc aagttccac tgaaaggtct tctttaaaat gacccactcc ccccaccaaa | 3240 |
| aaaagatgtt acattaaaat gcttgtgtgt gctcctaaat acaaacaagg tttaagaac | 3300 |
| aaacaaggta aaggagaaaa gtgtgaagca tggcagggaa gaacagaggt ggctcagccc | 3360 |
| catttccctc aggctaccca cagaaggctc aagaatgagc aactagcagt tggttaaaga | 3420 |
| tgaggctcaa attccaacca atcagggctg cacctcaatc gccaaccaaa atcataaagc | 3480 |
| cagtcagttg cagttcttcc cccagcagaa cacaggaagc atgaagacag agttttttgca | 3540 |
| ccatctcagt cttcatgatt gaaagcaaaa ccatgccagt gtgtcctgga aaatagcagc | 3600 |
| actgtgtcac agcgaggcac atgaaagcat cagtgctcaa ggcctcctgc tgtgtctacc | 3660 |
| acgctttccc tttccttctt ggatgagccg gtgcctgctc tgtatctact accaatcaga | 3720 |
| gcgagcacgg cttgatttca gctacccttt attacacacg tttgtgtaca tgtatgtcag | 3780 |
| aggacagcct gtaggacttg tgagtagacg cctttatcca ttgagccatg tcgctggtcc | 3840 |
| aatctgtcaa ctctctgtag tgtaagcatc ctctaaattg gaagctagtg tttcactttt | 3900 |

```
ttaagggagc tttggatgga aaataattct atttttaat aataaatttt ggtcttttta    3960
aatcttttgg tttttagata tatacctgca cttgctacaa agaaagctaa taattttaga    4020
aatttaaatg ttcaagcaag ctacagctta atatttacat gtagtaaaac caaagatcta    4080
gtttccttt aaaaaatat ggaagttctc cacgccccat ttcctttatt ataaagtaac     4140
tttttcttc actaacctga tactttctta tcatataaca cattcgttgc tgcagaataa    4200
actttgtaca ctgtaaatat gtataaacta ttctcattgg ttaataaaga gctgactggc   4260
ctagagctag gtgggagagg cagactagga gaattctggg aagaagggtg gagtcagaag   4320
tgtccccagc cagacagaga gggaacaaga cacactcgag aggtaaatac cacaagcctc   4380
agggcagcac atagattaat agaaatgggt tcatttaagt tataagagct agttaataat   4440
aagcctgagc tatcaactga gcatttaaaa ttaataagac tctctgactg gttacttggg   4500
agcggcttgc aggacaaaaa cttccaccaa ccatttattt cggaacacac agacccatgg   4560
atatgtgtgc ctattctag ctgcagaatt attttgatgg cactgacacc catacgggac    4620
caagcagtac atcctaagc ctggtgcatt gtagcttatc agtgaagttg tcattttcct    4680
tagtgaactt ttttctgcat cttttgtcaa gtttacacct gatgctctac gagtctagtg   4740
tctccttta cattacttaa ctatgtctta cgcccatctt tctttggtaa gctctcattg    4800
gtaattgttt tacctgtaca ttccttcatg ttaattttat atgcaaatga tcattttgtc   4860
tccagacagc aagtttcctt tcctccatta caatcccact accccaggtt ctgttccttt   4920
tgtcacttgc ataggccatg ctcttcactg ctgccctggt gcctggtgcc atgcgatggg   4980
ctgcacttgc tgaagataat ttcaaagcca tcttctaacc catgtgtccc tcttaaagtg   5040
gacgccagca ctgtcctctc tcctgacact aggcgcatgt gacctcccta caaaatgga    5100
agatagccaa gcgcccgcca tgtgtgggaa tgcagtgtcc tctagcgcct gccccatatc   5160
tcttgccttg ggaatacaga tgccagatgc agaaagacca cagcggccca cacagagacc   5220
acttggagaa attgtgtgta ggtttcccaa ctgattgcca accactgaca tcagatctca   5280
agacacagga atgaacacaa tttcagatga ctccaggcca cctcccgtga tagaatcacc   5340
acagctgagg aagtaaaagg gagagagaga ccgaacacca ttttctacag ccaactccct   5400
gacctcagaa tccttagtca tgagtgcgtt tataagcata caaagagga gtacagacga    5460
cagtcggttg gttcctaaca ggataaaagg ggtctctcct ccctgtaatt tgctaaacat   5520
catcatcagg aattcacatg gcctatcgag tgagactgtc acacagttct cgtaatcttg   5580
tgtcactcgg gagtcagggg tcatgggatg gtagccgtcc tgtcgcagct gggatggtag   5640
ccgtcctgtc gcagctggga tgaaccacct ggtaatgggg ctgctttctc tcatctgcta   5700
atatcctgtc tgagatggct agactacact gaaccaggaa tcacctctgg aacccctctc   5760
tcacagtatc ttcatctgac ttagatatca ggatggagct gggctctcag aactggctgg   5820
aaatagttcc ttttcttctg taattaaaag agatttcatc agaatgaaaa atctatttc    5880
ttacaacttg gtagaaaaaa atcataactt gcttagcaaa tcatctagga ctgttgcttg   5940
ctctgtggga agattcagtt tcttctaatt atgggacaat tcggacttt aattttcca     6000
gaagcttctg taaataatat ttttttctag aaaacctatt tttaaatggt tggcatacag   6060
ttattaacat tcatttcaaa tttaatttgg aaacaagctt gttttacctg tcaatcccag   6120
ttccctctcc ctaccctaac attcttcttg ttatcactat tttaatgtct gatttatctg   6180
ccattctttt cattttatat gtactgagcg atgtgttatt taaatcttct acatcctatg   6240
ggtctctact ttgtttcact ttttatctaa ttcaactcag gtgagttgaa acctttgcca   6300
```

-continued

```
cagtagcagc agagccaaca gcatctgggt tctagcaggt tagggaaggg ataaattcta    6360
gttttctact ggaaaacaaa cgactggaag tgattgtaag gtcagatgtg tgtgcgtcag    6420
ggtttagttc agtggttttg gttctctaac acactcattc agtctatttt agaaacacca    6480
gtcatctggc gtaagaaaag gtatgccatt tcatgacata aatcatctca agctttaaaa    6540
aatagtaatg ggaggggtgg aggatggtct gatggttagc gcactggctg ctcttgcaga    6600
ggtccagatt cggttcctag cacccacacg ggggctcaca actgcctgta cctccagttc    6660
ctaatgatct acaccctctt ctggcttcca caagcactgc acaaacttgg tgcacaaaca    6720
tgcacacaga taaaactcac acacacccac ataaacagta aaagtaaat aaaataataa     6780 caggcataaa ttacaagacc aacaacaaca aagaaaaaaa tgttcaaaat tacagtgaca    6840
aggcagaacc agcaagtgga tactataagg acttagtttt tagattttt ttttcgtgt      6900 gtgtgtgtgt gtgtgtgtgt gtgtgtgtgt gtgtgtgtgt gtgtgtgtgc gcgcgcgcac    6960
atgttcatgt cacaacaaga atgtgtaggt ccgtggaaac gttacaggag ctggttctct    7020
ccttccacta tgcaggttcc agggatcaaa cttagcagca agcaccaacc cccaaaactt    7080
ttcaatgtaa ccaatttaaa aatacaatgg aggcacatgg aagcacatgc acacctgcag    7140
atacacactt atgaacacac aagcacatag tatttgaaaa gaaaaaagaa aagcatccac    7200
ttgtggacta atgagcatga tcagaaaaat cacctatgct gtagttaaag tccccaaagg    7260
agaaggcatt gagattgcaa tgaagtaaat attgaaaaga gatggccaa aaacatctca     7320 ggattgatta gcaacaaacg acaagccaag caaagagaga caacccagca aaataaacac    7380
tggatgctct catcacccca atatgacatc aataaaacac aatccaaaga acccaaacgg    7440
cacagcgcgt gggaccctcc caaacggcac agcgcgtggg cctctacttc ctccacctcc    7500
aacctcccca aactgggacc tccccaaaca ggacccgagg ttcccctcta cttcctccac    7560
ctccaggaac atctgttatt cagtccttgc acatttcaag agtaaaaatg ttaaccatcg    7620
aatgagggaa taaatggcac agccagacta ccttgggatt gactggtttg tcccaacacc    7680
tggacttaag aagtgcacta ttagagcaac caacccagag aactagacct gaatacaaat    7740
ataaacactg tacacaaacc tcagacataa ttacagaact gtcttaccac acatcccta    7800 aaaaattcag atggtgcagt agcagaccca catataacag ttttctaaat tttgctttca    7860
aatgttgcca acattttgtc caattttatt gtcaaattaa tgtagaaata tttcgcaata    7920
atcctacttt ttctttgcat ttcaccatgt ttccttctgg cagaaagaaa tacatccaga    7980
ctgcacatgc catctttaaa ttgattttac atccactgta ctacaaaatt aagtataaag    8040
cttctaatga ccttacaatg gcactttgaa tggctccatt actaaccaaa tactccatca    8100
atatacaaat ttggttttgt gccaattatt aaatatctaa gacgtcttca tgcattggct    8160
ttgttttctt cttttaggtt ataaatttaa tgtaaactcc cagatactga gaaattaacc    8220
aaaaaaaaat ttatatatat atatatttt atatatatat atatatatat gtgaacaagg     8280
ttccaaagga gctaaactcc attac                                          8305
```

METHOD OF INTRODUCING TARGET-SPECIFIC FOREIGN GENE

CROSS-REFERENCE TO RELATED APPLICATIONS

This application is a U.S. National Phase of PCT Application No. PCT/JP2020/014980, filed Apr. 1, 2020, which claims the benefit of Japanese Patent Application No. 2019-070329, filed Apr. 2, 2019, each of which is incorporated herein by reference in its entirety.

REFERENCE TO SEQUENCE LISTING SUBMITTED ELECTRONICALLY

The content of the electronically submitted sequence listing (Name: 6663_0186 Sequence_Listing.txt; Size: 26.1 KB; and Date of Creation: Sep. 29, 2021) filed with the application is incorporated herein by reference in its entirety.

TECHNICAL FIELD

The present disclosure relates to methods for introducing an exogenous DNA into the genome of an animal cell in a target-specific manner, transformed cells obtained by using these methods, and methods for producing a polypeptide encoded by the exogenous DNA.

BACKGROUND ART

Methods of expressing a polypeptide such as a cytokine or an antibody in a cultured cell by a gene recombination technique and producing it in large quantities are well known. Such polypeptide production techniques generally include steps of introducing a polynucleotide encoding a polypeptide of interest into a cell in an expressible form to create a transformed cell and recovering the accumulated polypeptide of interest from a culture thereof. Widely-used as cells to be transformed are cells of microorganisms, insects, plants, or animals. Among them, animal cells are widely used as suitable host cells for obtaining polypeptides derived from animals. By expressing a polypeptide in animal cells, it is expected that post-translational modifications such as glycosylation and folding of the polypeptide will happen in a manner closer to the environment in which the polypeptide is produced in the living body.

When expressing an exogenous DNA in an animal cell, it is common to transform the animal cell with an expression vector incorporating a polynucleotide encoding the polypeptide of interest. However, unlike when introduced into the genome, an exogenous DNA introduced into a cell as an expression vector generally does not replicate and is not inherited through cell division, and thus it is difficult to stably retain its traits. Therefore, even though transformation with an expression vector is useful for use in an experimental environment for transient expression, it leaves issues for application in industrial production.

By introducing an exogenous DNA into the genome of animal cells, it becomes possible to stably retain traits derived from the expression vector. This is because polynucleotides introduced into the genome are highly likely to be replicated through cell division and retained stably. Based on this idea, it has become possible to stably produce many biological substances on an industrial scale using animal cells as a platform.

However, it has become clear that even when exogenous DNA is introduced into the genome, transformed cells with high expression levels cannot always be obtained. The expression level of exogenous DNA introduced into the genome generally differs depending on the position of introduction, and it has not always been possible to efficiently select desired transformed cells.

Targeted integration (TI) has been proposed as one of the techniques capable of solving the problems in introducing exogenous DNA into the genome (PTL 1-3). In TI, a genomic region suitable for introduction and expression of exogenous DNA is identified in advance, and the exogenous DNA to be expressed is site-specifically integrated into the identified genomic region. TI can be said to be a new gene recombination technology created with the improvement of genomic site-specific recombination technologies. As a result of TI, the predictability of the expression level of exogenous DNA and such of the obtained transformed cells has increased, and efficient acquisition of transformed cells having the required traits can be expected. In TI, genomic regions suitable for introducing exogenous DNA are often referred to as hotspots. So far, hotspots have been found in wide-ranging regions on genomes in various cells used as host cells for transformation. Moreover, an attempt to apply TI to the production of monoclonal antibodies by animal cells to obtain transformed cells useful for the production has also been reported (PTL 4, NPL 1-2).

CITATION LIST

Patent Literature

[PTL 1] International Publication No. WO 2008/151219
[PTL 2] International Publication No. WO 2013/190032
[PTL 3] International Publication No. WO 2016/064999
[PTL 4] International Publication No. WO 2017/184831

Non-Patent Literature

[NPL 1] Biotechnol. Prog., 2015, Vol. 31, No. 6, pp 1645-1656
[NPL 2] Methods 95 (2016) pp 3-12

SUMMARY OF INVENTION

Technical Problem

An objective of the present disclosure is to provide a new hotspot that is useful for Targeted Integration (TI).

Solution to Problem

The present inventors continued to search for regions that enable expression at a high level of exogenous DNA encoding a polypeptide such as an antibody in animal cells. In the production of transformed cells by TI reported so far, the initial expression level could not always be maintained for a long period of time, and there were times when the expression level would eventually decrease during culture (PLOS ONE, 2017 12(6): e0179902, Biotechnology Letters, 2018, Volume 40, Issue 8, pp 1209-1218). When such transformed cells are used for producing a polypeptide, the production amount of the expression product becomes unstable, and the production efficiency could decrease. Alternatively, if the transformed cells are unable to maintain industrial production levels, the production line would need to be restructured. The present inventors suspected that the decrease in the expression level of a polypeptide in culture may occur depending on the genomic integration site of the exogenous polynucleotide. Therefore, as a result of trying to search for hotspots that can be expected to maintain the expression level of exogenous DNA for a long period of time, the present inventors succeeded in finding a new hotspot, and achieved the present disclosure.

The present disclosure specifically encompasses the following embodiments:

[1] a method for introducing an exogenous DNA encoding a polypeptide of interest into a CHO cell, wherein the method comprises introducing the exogenous DNA into the genomic region specified by NCBI accession number NW_003614838.1 in the CHO cell;

[2] the method according to [1], wherein the integration site of the exogenous DNA is selected from a region comprising the coiled-coil domain-containing protein 91 (CCDC91) gene and its promoter region in the genomic region specified by NCBI accession number NW_003614838.1;

[3] the method according to [2], wherein the integration site of the exogenous DNA is selected from the CCDC91 gene region;

[4] the method according to [3], wherein the integration site of the exogenous DNA is in the first intron of the CCDC91 gene;

[5] the method according to any of [1] to [4], wherein the exogenous DNA is site-specifically introduced into the genomic region by any method selected from homologous recombination, recombinase-mediated cassette exchange (RMCE), and genome editing;

[6] the method according to any of [1] to [5], wherein the polypeptide of interest is an antigen-binding molecule;

[7] the method according to [6], wherein the antigen-binding molecule is an antibody;

[8] a method for producing a CHO cell or a CHO cell line, wherein the method comprises introducing an exogenous DNA encoding a polypeptide of interest into the genomic region specified by NCBI accession number NW_003614838.1 in the CHO cell;

[9] the method according to [8], wherein the integration site of the exogenous DNA is selected from a region comprising the coiled-coil domain-containing protein 91 (CCDC91) gene and its promoter region in the genomic region specified by NCBI accession number NW_003614838.1;

[10] the method according to [9], wherein the integration site of the exogenous DNA is selected from the CCDC91 gene region;

[11] the method according to [10], wherein the integration site of the exogenous DNA is in the first intron of the CCDC91 gene;

[12] the method according to any of [8] to [11], wherein the exogenous DNA is site-specifically introduced into the genomic region by any method selected from homologous recombination, recombinase-mediated cassette exchange (RMCE), and genome editing;

[13] the method according to any of [8] to [12], wherein the polypeptide of interest is an antigen-binding molecule;

[14] the method according to [13], wherein the antigen-binding molecule is an antibody;

[15] a method for producing a CHO cell or a CHO cell line, wherein the method comprises introducing a DNA cassette for introducing an exogenous DNA by an exchange reaction into the genomic region specified by NCBI accession number NW_003614838.1 in the CHO cell;

[16] the method according to [15], wherein the integration site of the DNA cassette is selected from a region comprising the coiled-coil domain-containing protein 91 (CCDC91) gene and its promoter region in the genomic region specified by NCBI accession number NW_003614838.1;

[17] the method according to [16], wherein the integration site of the DNA cassette is selected from the CCDC91 gene region;

[18] the method according to [17], wherein the integration site of the DNA cassette is in the first intron of the CCDC91 gene;

[19] the method according to any of [15] to [18], wherein the exogenous DNA is an exogenous DNA encoding an antigen-binding molecule of interest;

[20] the method according to [19], wherein the antigen-binding molecule is an antibody;

[21] an isolated CHO cell comprising an exogenous DNA encoding a polypeptide of interest introduced into the genomic region specified by NCBI accession number NW_003614838.1;

[22] the CHO cell according to [21], wherein the integration site of the exogenous DNA is selected from a region comprising the coiled-coil domain-containing protein 91 (CCDC91) gene and its promoter region in the genomic region specified by NCBI accession number NW_003614838.1;

[23] the CHO cell according to [22], wherein the integration site of the exogenous DNA is selected from the CCDC91 gene region;

[24] the CHO cell according to [23], wherein the integration site of the exogenous DNA is in the first intron of the CCDC91 gene;

[25] the method according to any of [21] to [24], wherein the exogenous DNA is site-specifically introduced into the genomic region by any method selected from homologous recombination, recombinase-mediated cassette exchange (RMCE), and genome editing;

[26] the CHO cell according to any of [21] to [25], wherein the polypeptide of interest is an antigen-binding molecule;

[27] the CHO cell according to [26], wherein the antigen-binding molecule is an antibody;

[28] an isolated CHO cell comprising a DNA cassette for introducing an exogenous DNA into the genomic region specified by NCBI accession number NW_003614838.1 by an exchange reaction;

[29] the CHO cell according to [28], wherein the integration site of the DNA cassette is selected from a region comprising the coiled-coil domain-containing protein 91 (CCDC91) gene and its promoter region in the genomic region specified by NCBI accession number NW_003614838.1;

[30] the CHO cell according to [29], wherein the integration site of the DNA cassette is selected from the CCDC91 gene region;

[31] the CHO cell according to [30], wherein the integration site of the DNA cassette is in the first intron of the CCDC91 gene;

[32] the CHO cell according to any of [28] to [31], wherein the exogenous DNA is an exogenous DNA encoding an antigen-binding molecule of interest;

[33] the CHO cell according to [32], wherein the antigen-binding molecule is an antibody;

[34] a method for producing a polypeptide, wherein the method uses a CHO cell in which an exogenous DNA encoding a polypeptide of interest is introduced into the genomic region specified by NCBI accession number NW_003614838.1;

[35] the method according to [34], wherein the integration site of the exogenous DNA is selected from a region comprising the coiled-coil domain-containing protein 91 (CCDC91) gene and its promoter region in the genomic region specified by NCBI accession number NW_003614838.1;

[36] the method according to [35], wherein the integration site of the exogenous DNA is selected from the CCDC91 gene region;

[37] the method according to [36], wherein the integration site of the exogenous DNA is in the first intron of the CCDC91 gene;

[38] the method according to [37], wherein the exogenous DNA is site-specifically introduced into the genomic region by any method selected from homologous recombination, recombinase-mediated cassette exchange (RMCE), and genome editing;

[39] the method according to any of [34] to [38], wherein the polypeptide of interest is an antigen-binding molecule;

[40] the method according to [39], wherein the antigen-binding molecule is an antibody;

[41] a method for producing a polypeptide comprising the following steps of:
  (1) introducing an exogenous DNA encoding a polypeptide of interest into a CHO cell, wherein the exogenous DNA is introduced into the genomic region specified by NCBI accession number NW_003614838.1 of the genome of the CHO cell;
  (2) culturing the CHO cell into which the exogenous DNA has been introduced; and
  (3) recovering the polypeptide of interest;

[42] the method according to [41], wherein the integration site of the exogenous DNA is selected from a region comprising the coiled-coil domain-containing protein 91 (CCDC91) gene and its promoter region in the genomic region specified by NCBI accession number NW_003614838.1;

[43] the method according to [42], wherein the integration site of the exogenous DNA is selected from the CCDC91 gene region;

[44] the method according to [43], wherein the integration site of the exogenous DNA is in the first intron of the CCDC91 gene;

[45] the method according to [41], wherein the step of introducing the exogenous DNA encoding the polypeptide of interest into the CHO cell includes the following steps (i)-(ii):
  (i) introducing into the CHO cell a DNA cassette for introducing the exogenous DNA by an exchange reaction; and
  (ii) introducing the exogenous DNA into the genomic region specified by NCBI accession number NW_003614838.1 by a recombinase which recognizes the DNA cassette of (i) as a target site;

[46] the method according to any of [41] to [45], wherein the polypeptide of interest is an antigen-binding molecule; and

[47] the method according to [46], wherein the antigen-binding molecule is an antibody.

Effects of the Invention

Through this disclosure, a hotspot suitable for obtaining animal cells transformed by TI was discovered. In a preferred embodiment, the hotspot provided by the present disclosure can stably maintain the expression level of a polypeptide encoded by an exogenous DNA introduced into its region over a long period of time.

DESCRIPTION OF EMBODIMENTS

Figure 1:
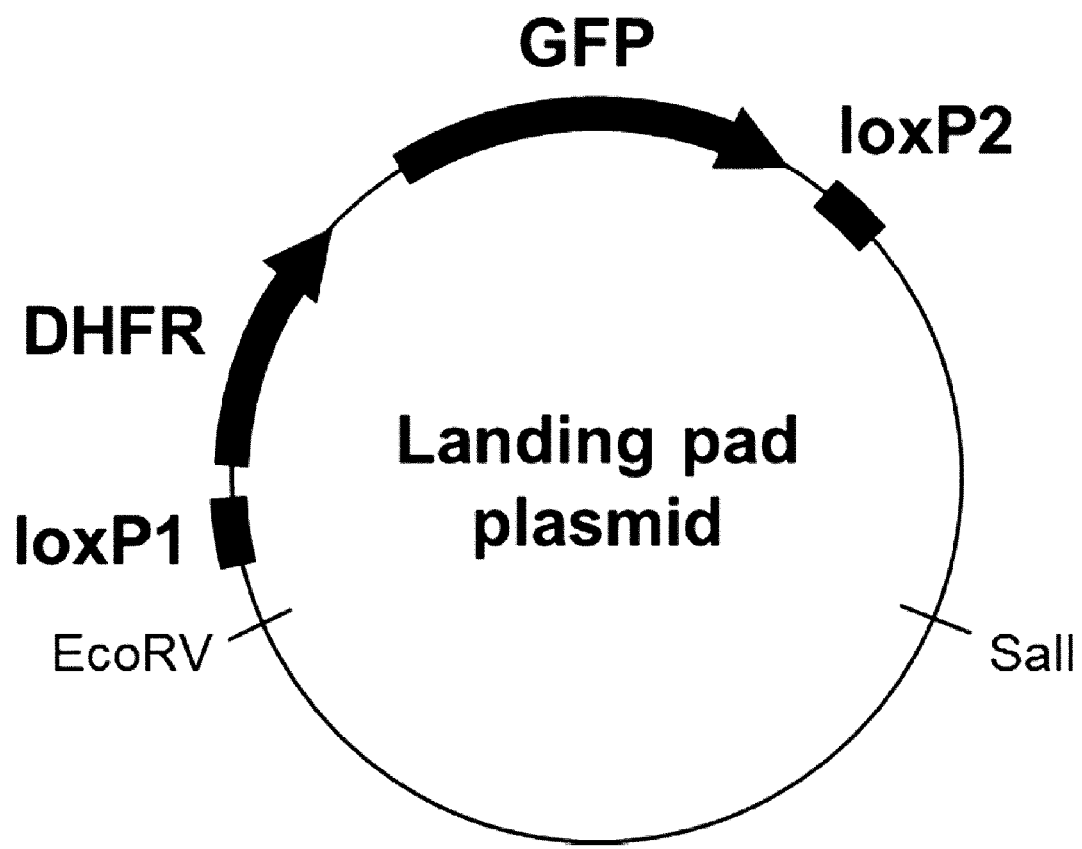
FIG. 1 shows a map of a landing pad used in the search for a hotspot. Genes encoding dihydrofolate reductase (DHFR), which is a selection marker for transformed cells, and green fluorescent protein (GFP), which is a marker for screening cells with a high expression, have been integrated. Recognition sequences (loxP1 and loxP2) of the recombinase Cre are inserted at the two ends of these two genes to form a DNA cassette.

Hereinafter, embodiments for carrying out the present invention will be described in more detail.

The following definitions and detailed descriptions are provided to facilitate the understanding of the present disclosure explained herein.

In the present specification, the "antigen-binding molecule" is limited only by binding to the antigen of interest. The antigen-binding molecule can be a domain having any structure as long as the domain used binds to the antigen of interest. Examples of such a domain include, but are not limited to, an antibody heavy chain variable region (VH), an antibody light chain variable region (VL), a single-domain antibody (sdAb), a module called A domain of approximately 35 amino acids contained in an in vivo cell membrane protein avimer (WO2004/044011 and WO2005/040229), adnectin containing a 10Fn3 domain serving as a protein binding domain derived from a glycoprotein fibronectin expressed on cell membranes (WO2002/032925), Affibody containing an IgG binding domain scaffold constituting a three-helix bundle composed of 58 amino acids of protein A (WO1995/001937), DARPins (designed ankyrin repeat proteins) which are molecular surface-exposed regions of ankyrin repeats (AR) each having a 33-amino acid residue structure folded into a subunit of a turn, two antiparallel helices, and a loop (WO2002/020565), anticalin having four loop regions connecting eight antiparallel strands bent toward the central axis in one end of a barrel structure highly conserved in lipocalin molecules such as neutrophil gelatinase-associated lipocalin (NGAL) (WO2003/029462), and a depressed region in the internal parallel sheet structure of a horseshoe-shaped fold composed of repeated leucine-rich-repeat (LRR) modules of an immunoglobulin structure-free variable lymphocyte receptor (VLR) as seen in the acquired immune systems of jawless vertebrates such as lamprey or hagfish (WO2008/016854).

Preferred examples of the antigen-binding molecule of the present invention include an antigen-binding molecule that can exert an antigen binding function by a molecule constituted only by the antigen-binding domain, and an antigen-binding molecule that can exert an antigen binding function by itself after being released from an additional peptide linked thereto. Examples of such an antigen-binding molecule include, but are not limited to, single-domain antibodies, scFv, Fv, Fab, Fab', and F(ab')$_2$.

One preferred example of the antigen-binding molecule of the present invention includes an antigen-binding molecule having a molecular weight of 60 kDa or smaller. Examples of such an antigen-binding molecule include, but are not limited to, single-domain antibodies, scFv, Fab, and Fab'. The antigen-binding molecule having a molecular weight of 60 kDa or smaller is usually likely to be subjected to clearance by the kidney when existing as a monomer in blood (see J Biol Chem. 1988 Oct. 15; 263 (29): 15064-70).

Antibodies

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

Antibody Fragments

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g., scFv); and multispecific antibodies formed from antibody fragments. As such, antibodies and antibody fragments are representative examples of antigen binding molecules.

Fc Regions

The term "Fc region" herein is used to define a C-terminal region of an immunoglobulin heavy chain that contains at least a portion of the constant region. The term includes native sequence Fc regions and mutant Fc regions. In one embodiment, a human IgG heavy chain Fc region extends from Cys226, or from Pro230, to the carboxyl-terminus of the heavy chain. However, the C-terminal lysine (Lys447) or glycine-lysine (residues 446-447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, MD, 1991.

Nucleic Acids/Polynucleotides

An "isolated" nucleic acid/polynucleotide refers to a nucleic acid/polynucleotide molecule that has been separated from a component of its natural environment. An isolated nucleic acid/polynucleotide includes a nucleic acid/polynucleotide molecule contained in cells that ordinarily contain the nucleic acid/polynucleotide molecule, but the nucleic acid/polynucleotide molecule is present extrachromosomally or at a chromosomal location that is different from its natural chromosomal location. In the present disclosure, a nucleic acid/polynucleotide is exogenous to the host cell when it is obtained from an environment other than the host cell (endogenous), regardless of whether the nucleic acid/polynucleotide has been artificially constructed or was naturally occurring. Thus, for example, when a nucleic acid/polynucleotide contains a cDNA, the nucleic acid/polynucleotide is usually exogenous to the host cell.

When an exogenous nucleic acid/polynucleotide of the present disclosure contains DNA, it is particularly described as "exogenous DNA". The exogenous DNA can also contain components other than DNA if it retains the required genetic information. For example, a DNA complexed with a component other than DNA, such as a protein or a liposome constituting a virus particle, is also an exogenous DNA. In the present disclosure, the host cell is a Chinese hamster (*Cricetulus griseus*, Japanese name is Mongol Kinuge Nezumi) cell. Therefore, a DNA containing a nucleotide sequence information that is not normally contained in the genome thereof can be referred to as an "exogenous DNA".

The nucleotide sequence information of the Chinese hamster genome can be obtained, for example, as a GenBank reference sequence. If the nucleotide sequence information of a given DNA contains a nucleotide sequence that does not match the reference sequence, even partially, it can be understood that it is an exogenous DNA. For example, a DNA containing the genetic information of the Chinese hamster itself, while a part of it has been modified into genetic information derived from another species or an artificial information, is included in exogenous DNAs. As such, a large part of the exogenous DNAs becomes exogenous by containing artificially-constructed nucleotide sequence information. When a given DNA encodes an amino acid sequence, and the original amino acid sequence information is maintained even after the nucleotide sequence of the DNA is modified, it is an artificially-constructed DNA. Alternatively, DNA from which introns contained in the genomic sequence have been removed from the Chinese hamster gene (e.g., a cDNA) is also usually exogenous.

Vectors

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors can direct the expression of nucleic acids to which they are operatively linked. Such vectors are referred to herein as "expression vectors."

Host Cells

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that has the same function or biological activity as screened or selected for in the originally transformed cell are included herein.

In a certain embodiment, the present disclosure provides a method for introducing an exogenous DNA encoding a polypeptide of interest into a CHO cell, wherein the method comprises site-specifically introducing the exogenous DNA into a genomic region specified by NCBI accession number NW_003614838.1 of the CHO cell genome.

CHO cells (Chinese Hamster Ovary Cell) are a general term for a fibroblast cell line established from the ovaries of Chinese hamsters. They have excellent proliferative ability and can be cultured in an artificial medium by an adhesive culture or suspension culture. Various polypeptides are produced by genetic recombination using CHO cells as a host. For example, dhfr-CHO lacking the DHFR gene (Proc. Natl. Acad. Sci. USA (1980) 77, 4216-4220) and CHO-K1 (Proc. Natl. Acad. Sci. USA (1968) 60, 1275) are widely used as host cells in genetic recombination technology. Mutant lines of these CHO cells are also included in the CHO cells of the present disclosure. In addition, as cells derived from CHO cells, CHO-DG44 and CHO-DXB11 lines are being used as host cells. These known cell lines derived from CHO cells are also included in the CHO cells in the present disclosure.

The CHO cells constituting the present disclosure can be obtained from cell banks such as ATCC or as a commercially distributed and available cell line. When a CHO cell theoretically consists of a group of cells established from a single cell, it is particularly referred to as a "CHO cell line". In the present disclosure, "CHO cells" may be a CHO cell line unless otherwise specified.

In the present disclosure, the genomic region identified as a hotspot is specified by NCBI accession number NW_003614838.1 in the genome of CHO cells. NW_003614838.1 is a CHO cell genomic nucleotide sequence revealed by the whole genome shotgun sequence method, and consists of about 465.6 kbp. Therefore, in the present disclosure, the region into which the exogenous DNA is introduced may be any location within the approximately 465.6 kbp.

In the nucleotide sequence, a preferable integration site in the present disclosure includes, for example, a region specified by a sequence existing on the LOC103164262 (coiled-coil domain-containing protein 91; CCDC91) gene and its promoter. In a certain embodiment, this region consists of approximately 159.4 kbp containing the gene and its promoter region. Alternatively, in another embodiment, a nucleotide sequence of about 121.3 kbp not containing the promoter in this region is also preferable as the integration site of the exogenous DNA. For example, in the nucleotide sequence constituting the CCDC91 gene, a range of about 20 kbp including 10 kbp upstream and downstream of the first intron, or a range of about 10 kbp including 5 kbp upstream and downstream of the first intron is preferable as a region to introduce an exogenous DNA in the present disclosure. As an example, the nucleotide sequences 5 kbp upstream and downstream of the first intron are shown in SEQ ID NOs: 1 and 2, respectively. Therefore, the relationship between each SEQ ID NO and the integration site can be shown, for example, as follows:

5'-(SEQ ID NO: 1)-[Integration site (i.e., hotspot)]-(SEQ ID NO: 2)-3'

Here, when the nucleotide sequence constituting the CCDC91 gene is mapped on the nucleotide sequence of the genome, it is located in the reverse complementary sequence (that is, the antisense sequence) when viewed from the genome sequence. Therefore, in the nucleotide sequence of the CCDC91 gene, the first intron is mapped over the region including the 5'end of SEQ ID NO: 2 (positions 1-6454 in SEQ ID NO: 2) to the region including the 3'end of SEQ ID NO: 1 (positions 3190-5040 in SEQ ID NO: 1). The nucleotide sequence of the first intron in which both are linked is shown in SEQ ID NO: 3. Therefore, in a preferred embodiment of the present disclosure, the site-specific integration site of exogenous DNA can be selected from the region specified by the nucleotide sequence of SEQ ID NO: 3 (reverse complementary sequence) on the CHO cell genome.

In the present disclosure, a region specified by a certain nucleotide sequence includes the case where a plurality of nucleotide sequences are homologous. That is, even if the target nucleotide sequence X contains some mutations or modifications, if it is homologous to a nucleotide sequence A as a whole, it is a "region specified by nucleotide sequence A". When a plurality of nucleotide sequences are homologous, they can usually be aligned. By aligning the differing nucleotide sequence A and nucleotide sequence X, a position corresponding to a specific position in nucleotide sequence A can be specified on nucleotide sequence X. Algorithms for aligning multiple nucleotide sequences are known. BLASTN, for example, is one of the common tools for aligning nucleotide sequences. Nucleotide sequences that can be regarded as being homologous to NCBI accession number NW_003614838.1, the CCDC91 gene and its promoter, the first intron, and the like according to these known algorithms correspond to "regions specified by each nucleotide sequence" in the present disclosure.

As described above, there are several cell lines known to have different properties such as drug resistance and nutritional requirement in CHO cells. If these differences in properties are caused by mutations or modifications in the nucleotide sequence information of the genome, and even if they occur in the regions specified by the present disclosure, they are "regions specified by each nucleotide sequence" if the regions can be identified. Mutations and modifications of genomic nucleotide sequence information include additions, deletions, insertions, and substitutions of nucleotide sequence information. Alternatively, changes in nucleotide sequence information that are not accompanied by apparent cellular trait changes (such as polymorphism) can be tolerated. In addition, if the nucleotide sequence information is maintained, differences in epigenetic modification states between DNAs, such as DNA methylation, are also tolerated.

In the present disclosure, exogenous DNA can be site-specifically introduced into the above region by a known homologous recombination technique or genome editing technique. "Site-specific" refers to selecting a position specified by a certain nucleotide sequence in the nucleotide sequence constituting the genome as a position for introduction, and introducing a DNA of interest using this position as a target. Therefore, "site-specific" can also be expressed as "targeting". In the present disclosure, introduction of nucleic acids/polynucleotides into the genome can be achieved by inserting a DNA at a target site or replacing a portion of the genome with the DNA to be introduced.

For example, the following methods are known as methods used for incorporating an exogenous DNA by TI:
homologous recombination,
RMCE (recombinase-mediated cassette exchange), and gene editing.

Homologous recombination is a method that utilizes the DNA repair mechanism that cells originally have. Exogenous DNA having a nucleotide sequence homologous to the target position on the genome is introduced into cells to replace the DNA existing at the target position with the exogenous DNA. In homologous recombination, the efficiency is generally very low (about 10-5 to 10-7%) because a special enzyme that specifically recognizes the nucleotide sequence is not artificially used.

RMCE is the method used in the Examples of the present invention, and is a gene transfer method which uses a recombinase and the nucleotide sequence it recognizes. By introducing in advance, the recognition nucleotide sequence of the recombinase into the target position on the genome and introducing an exogenous DNA similarly having the recognition nucleotide sequence into the cell, the DNA existing at the target position and the exogenous DNA are substituted. Typical recombinase/recognition sequence combinations are "Cre/loxP" and "FLP/FRT", but there are several others as well.

Gene editing (genome editing) is a gene transfer method that uses genome editing technology that can target and cleave a target position on the genome. An enzyme designed to target a target position on the genome is introduced into a cell, and the target position is cleaved to promote DNA repair in the cell. At this time, by introducing an exogenous DNA together with the enzyme, the exogenous DNA is easily linked to the cleavage site. CRISPR/Cas, TALEN, and ZFN are representative enzymes used in genome editing technology. For example, CRISPR-Cas9, a representative genome editing tool, recognizes a nucleotide sequence complementary to a guide RNA and cleaves double-stranded DNA (namely, genomic DNA). If the donor vector is co-introduced, the exogenous DNA loaded on the vector can be introduced into the double-stranded DNA in the process of repairing the cleaved double-stranded DNA.

Therefore, by using a guide RNA corresponding to the nucleotide sequence of the above-mentioned integration site, an exogenous DNA can be introduced in a site-specific manner using CRISPR-Cas9.

In the present disclosure, the integration site of exogenous DNA is specified by NCBI accession number NW_003614838.1. Furthermore, in identifying the integration site, as already described, the integration site can be identified from among nucleotide sequences homologous to the nucleotide sequence referred to with NCBI accession number NW_003614838.1. Here, when designing a guide RNA for introducing an exogenous DNA into an above-mentioned homologous nucleotide sequence, the nucleotide sequence of the genome of the CHO cell into which DNA is planned to be introduced can be determined in advance. By considering not only the reference sequence, but also the genomic nucleotide sequence of the specific CHO cell into which the actual introduction is planned, more specific design of nucleotide sequences becomes possible.

In a certain embodiment of the present disclosure, the donor vector can include any element, such as a selection marker, in addition to the exogenous DNA to be introduced. Selection markers include antibiotic resistance genes and metabolic selection markers. By placing the genome-edited CHO cells under culture conditions appropriate for the selection marker, cells into which the exogenous DNA loaded on the donor vector has been introduced into the genome in an expressible state can be selectively maintained and proliferated. A cell population selectively maintained through the above steps constitutes a cell population in which a common exogenous DNA is introduced at the same position in the CHO cell genome. Alternatively, if the expression level of exogenous DNA in the resulting cell population is compared and transformed cells that exceed the desired expression level are screened and cloned, it is also possible to establish the transformed cells into which the exogenous DNA has been integrated into the hotspot identified in the present disclosure as a cell line. The method for introducing exogenous DNA provided in the present disclosure is useful for producing CHO cells or CHO cell lines.

In other words, the present disclosure provides a method for producing CHO cells or a CHO cell line, wherein the method comprises selectively introducing an exogenous DNA encoding a polypeptide of interest into the region in the CHO cell genome identified by NCBI accession number NW_003614838.1. The method of the present disclosure can further additionally include determining the expression level of the introduced exogenous DNA and comparing the determined expression level. After comparing the expression levels, more desirable transformed cells can be obtained by selecting and cloning cells having high expression levels. The expression levels of exogenous DNA in all transformed cells can be ranked, and transformed cells included in, for example, the top 20%, or 10%, preferably 8%, or more preferably 5% can be selected as the desirable transformed cells.

When a DNA encoding a polypeptide that generates a signal is used as the exogenous DNA, transformed cells can be screened by comparing the expression level using signal intensity as an index. Signal-generating polypeptides include the green fluorescent protein (GFP) and its derivatives. Alternatively, a selection marker can be used as the exogenous DNA. When a selection marker is used, CHO cells can be cultured under culture conditions suitable for the marker, and CHO cells into which the exogenous DNA has been introduced into the hotspot identified by the present disclosure can also be selected. Nucleic acids/polynucleotides encoding the selection markers, signal-generating polypeptides, and such that are integrated into the genome from the donor vector can also be linked to form a DNA cassette.

In the present disclosure, "landing pad" is a DNA comprising the above-mentioned "DNA cassette", and is synonymous with "DNA cassette" in that it introduces an exogenous DNA into the genome.

When introducing a DNA cassette of the donor vector into the genome hotspot according to the present disclosure, a recognition sequence of the recombinase can be further additionally added to the DNA cassette. Cre recombinase and FLP recombinase are known as recombinases. These recombinases recognize their respective recognition sequences, loxP and FRT. Therefore, by adding these recognition sequences to both ends of the DNA cassette, the exogenous nucleic acid/polynucleotide introduced by the DNA cassette can be easily and selectively replaced with another DNA by a recombination reaction. Recombining (substituting) an exogenous DNA once introduced into the genome with a different DNA cassette is called an exchange reaction. The nucleotide sequence selectively recognized by the recombinase involved in the exchange reaction can be referred to as a recombination targeting sequence.

Once established, the transformed cells according to the present disclosure can express an arbitrary polypeptide by substituting the exogenous DNA incorporated into the hotspot with a DNA encoding an arbitrary exogenous polypeptide. Furthermore, in transformed cells in which the DNA cassette has been introduced into the hotspot and which can express exogenous DNA at a high level, even after the exogenous DNA in the DNA cassette is substituted with another exogenous DNA, a high expression level equivalent to that of the exogenous DNA before the substitution can be expected. As such, transformed cells established according to the present disclosure are useful as parent cells (master cells) because they can be applied to the production of an arbitrary polypeptide. That is, the present disclosure provides a method for producing CHO cells or a CHO cell line, wherein the method comprises inserting a DNA cassette for introducing an exogenous DNA by an exchange reaction into the genomic region specified by NCBI accession number NW_003614838.1 of CHO cells.

The present disclosure also relates to isolated CHO cells comprising an exogenous DNA introduced into the region specified by NCBI accession number NW_003614838.1 of the genome. In a preferred embodiment, the CHO cells of the present disclosure can include a recombination targeting site for introducing an arbitrary DNA using an exogenous DNA. That is, the present disclosure relates to isolated CHO cells comprising a DNA cassette for introducing an exogenous DNA by an exchange reaction into the genomic region specified by NCBI accession number NW_003614838.1. The incorporation of exogenous DNA into a specific region in the genome retained by CHO cells can be verified, for example, by amplifying the genomic DNA as a template using primers comprising nucleotide sequences specific to the nucleotide sequences constituting the region. If a product having a desired nucleotide sequence length can be confirmed as a result of amplification, it is possible to know that the CHO cell has an exogenous DNA integrated into the target region.

In the present disclosure, "isolated" refers to a cell or cell population isolated from at least some components of its natural environment, such as a substantially homogeneous cell population. "Substantially homogeneous" means that the frequency of the number of cells having the characteristics of the present disclosure in the cell population is 1/20 or more, preferably 1/10 or more, more preferably 1/5 or more, still more preferably 1/3 or more, even more preferably 1/2 or more, and most preferably 1/1. Here, a cell with the features of the present disclosure is usually defined by comprising an exogenous DNA introduced into the region identified by NCBI accession number NW_003614838.1 of the genome.

The exogenous DNA incorporated into the hotspot as a DNA cassette is then substituted with a DNA encoding an arbitrary polypeptide to produce an arbitrary polypeptide. In the present disclosure, the polypeptide intended for production is optional. For example, various polypeptides conventionally produced by culturing CHO cells can be applied to the present disclosure. Therefore, the present disclosure provides, in a certain embodiment, a method for producing a polypeptide using CHO cells into which an exogenous DNA encoding a polypeptide of interest has been introduced into the genomic region specified by NCBI accession number NW_003614838.1. In the present disclosure, the method for producing a polypeptide can preferably include the following steps of:

(1) introducing an exogenous DNA encoding a polypeptide of interest into a CHO cell, wherein the exogenous DNA is site-specifically introduced into the genomic region specified by NCBI accession number NW_003614838.1 of the CHO cell genome;
(2) culturing the CHO cell into which the exogenous DNA has been introduced in (1); and
(3) recovering the polypeptide of interest.

In the present disclosure, the step of site-specific introduction into the genomic region specified by NCBI accession number NW_003614838.1 of the CHO cell genome is based on the nucleotide sequence-specific recombination reaction of the genome. A nucleotide sequence-specific recombination reaction means, in a preferred embodiment, site-specific introduction of an exogenous DNA of interest into a target site selected from the nucleotide sequence of the genome. In the present disclosure, site-specific introduction of an exogenous DNA into the genome includes the insertion of the exogenous DNA into the genome. Alternatively, a DNA of interest can be introduced into a target position by substituting a part of the nucleotide sequence constituting the genome with the exogenous DNA.

In the present disclosure, the exogenous DNA once site-specifically introduced can further be substituted with another DNA. A cell into which a recombinase recognition sequence for substitution has been introduced into a hotspot is useful as a parent cell (master cell) of the present disclosure.

The integration site and orientation of the exogenous DNA can be confirmed by analyzing the nucleotide sequence of the genome of the parent cell (master cell), or transformed cell in which the exogenous DNA in the genome has been replaced with an exogenous DNA encoding the polypeptide intended for production, and collating with the original genomic sequence, as necessary. For example, when genomic DNA is amplified by PCR with primers specific to the nucleotide sequences constituting the genomic region selected as the target (integration site), it is possible to selectively amplify the exogenous nucleic acid/polynucleotide and detect its presence. Alternatively, the nucleotide sequence of the amplification product can be determined to confirm the introduction of the exogenous nucleic acid/polynucleotide of interest.

Parent cells (master cells), or transformed cells in which the exogenous DNA in the genome has been replaced with an exogenous DNA encoding a polypeptide intended for production, can be divided into small portions after expansion culture and cryopreserved. In addition, the expression level of the exogenous DNA of the transformed cells thawed after cryopreservation and its stability can be evaluated to further select transformed cells that are advantageous for production. Alternatively, the transformed cells obtained according to the present disclosure can be adapted to conditions for producing the polypeptide to obtain cells advantageous for production.

Examples of polypeptides that can be applied to the production method of the present disclosure include cytokines, peptide hormones, growth factors, their receptors, antigen-binding molecules typified by antibodies, enzymes, and the like. These polypeptides can be expressed by introducing a polynucleotide encoding a full length or fragment into the genome, as necessary. Alternatively, they can be fused with an arbitrary polypeptide. They can also be expressed as partially-modified molecules, or as molecules in which multiple fragments have been artificially linked.

CHO cells into which an exogenous DNA encoding a polypeptide of interest has been introduced can be cultured under conditions suitable for CHO cells. For example, conditions for culturing in a commercially available basal medium (a basal medium for culturing animal cells) are widely known. For example, DMEM, MEM, RPMI1640, IMDM, F10 medium, F12 medium, and the like are known as culture solutions for animal cells. Animal serum can also be added to the medium, or a serum-free culture can also be adopted when possible. Regarding the specific CHO cell culture conditions, culture is typically carried out under an atmosphere with a $CO_2$ concentration in the gas phase of 0-40%, preferably 2-10%, at 30-39° C., preferably 37° C. or so, for 1-14 days. Alternatively, the culture can be continued for a longer period if the production of the polypeptide of interest continues. During the culture period, as necessary, a part or all the medium can be replaced with a new medium to recover the medium.

Culture can be carried out using, as the various culture apparatuses for culturing animal cells, for example, a fermenter-type tank culture apparatus, air lift-type culture apparatus, culture flask-type culture apparatus, spinner flask-type culture apparatus, microcarrier-type culture apparatus, fluidized bed-type culture apparatus, hollow fiber-type culture apparatus, roller bottle-type culture apparatus, filling tank-type culture apparatus, and the like.

If the polypeptide of interest is secreted into the culture, the polypeptide can be recovered by retrieving the culture supernatant. The polypeptide can be purified to a substantially pure and homogeneous state. Isolation and purification of the polypeptide can be done by applying isolation/purification methods used in conventional purification steps. For example, column chromatography, filtration, ultrafiltration, salting-out, solvent precipitation, solvent extraction, distillation, immunoprecipitation, SDS-polyacrylamide gel electrophoresis, isoelectric focusing, dialysis, recrystallization, and such are appropriately selected and combined to suitably isolate and purify antibodies. Chromatography includes affinity chromatography, ion exchange chromatography, hydrophobic chromatography, gel filtration chromatography, reverse phase chromatography, adsorption chromatography, and the like. These chromatographies are performed using liquid chromatography, such as HPLC and FPLC. A polypeptide containing an Fc domain, such as an antibody, can also be purified by affinity chromatography such as a protein A column or a protein G column. Examples of a protein A column include HYPER DR, POROS®, SEPHAROSE® F.F. (manufactured by Pharmacia), and the like.

EXAMPLES

The following are examples of methods and compositions of the invention. It is understood that various other embodiments may be practiced, given the general description provided above.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

Example 1

Preparation of Landing Pad Plasmid

A "landing pad" containing a DNA cassette that functions as a target position for introducing a gene of interest during the cassette exchange reaction was created and integrated into the plasmid (FIG. 1). This landing pad plasmid carries the green fluorescent protein (GFP) gene as a marker gene for identifying a gene high expression region on the CHO cell genome. It also has the dihydrofolate reductase (DHFR) gene as a selection marker after introduction of the landing pad plasmid. DNA sequences (loxP1 and loxP2) recognized by the recombinase Cre are inserted at both ends of the two genes, the DHFR gene and the GFP gene. The DHFR gene and GFP gene existing between these two loxPs are removed during the cassette exchange reaction and replaced with a gene encoding the polypeptide to be produced loaded on the recombination plasmid. In the following examples, antibody production was attempted by substituting with an antibody gene.

Example 2

Preparation of Recombination Plasmid

Figure 2:
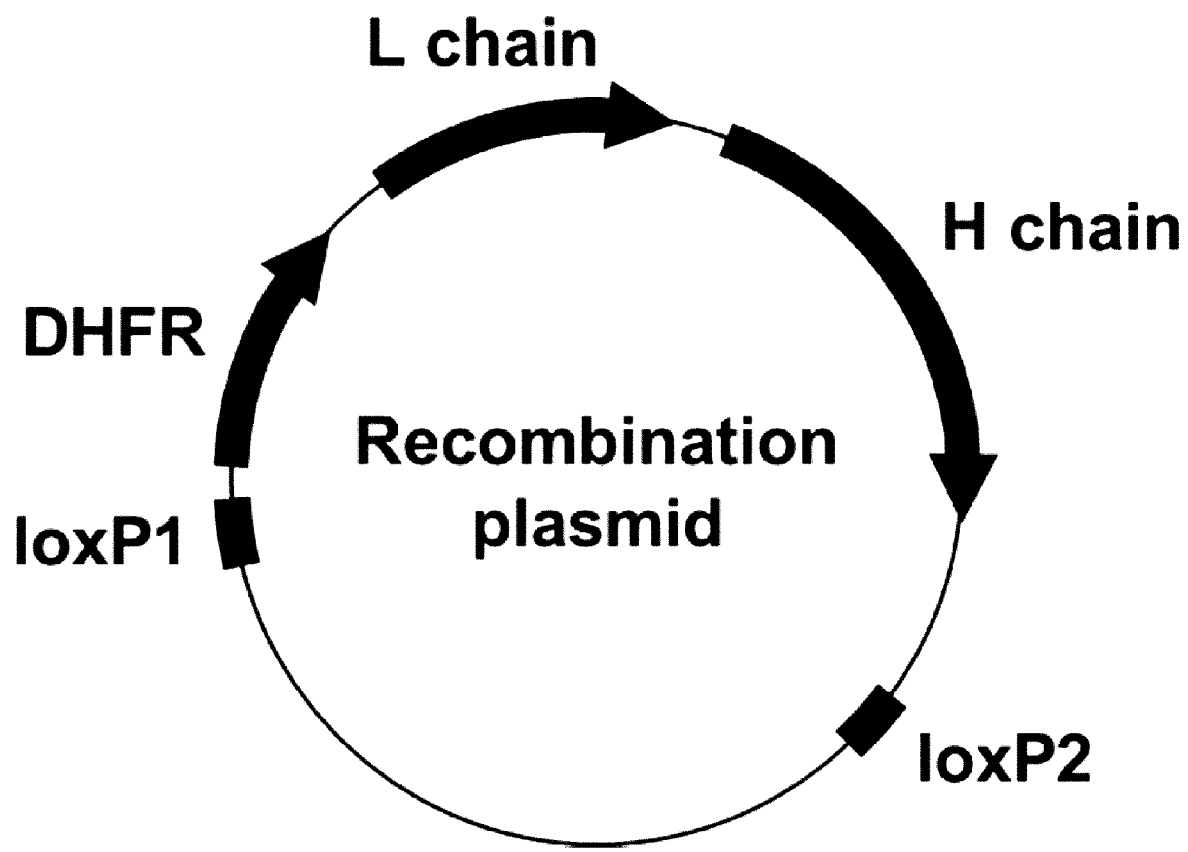
FIG. 2 shows a map of a recombination plasmid for a cassette exchange reaction with a landing pad DNA cassette integrated into the genome. The recombinase recognition sequence loxP is arranged at the two ends of the genes encoding the selection marker DHFR, the light chain (L), and the heavy chain (H) to form a DNA cassette.

A "recombination plasmid" was prepared for the cassette exchange reaction with the DNA cassette of the landing pad inserted on the CHO cell genome (FIG. 2). The recombination plasmid carries the DHFR gene and the antibody gene consisting of heavy and light chains, and loxP is inserted at both ends of these genes. As the evaluation antibody, one type of IgG1 antibody (mAb-A) and two types of IgG2 antibody (mAb-B, C) were used. Each antibody recognizes a different antigen as follows:

mAb-A: GYM329/Anti-latent myostatin antibody/IgG1;
mAb-B: CIM331/Anti-IL-31 receptor antibody/IgG2 (WO 2010/064697);
mAb-C: SA237/Anti-IL-6 receptor antibody/IgG2 (WO 2016/027859).

Although FIG. 2 uses a recombination plasmid carrying an antibody gene consisting of one set of heavy chain/light chain, the configuration of the recombination plasmid can be appropriately modified depending on the type of the antibody to be expressed, such as loading an antibody gene consisting of two sets of heavy chain/light chain in the case of a bispecific antibody.

Example 3

Preparation of a Host Cell for Targeted Integration (TI)

Transfection of the landing pad plasmid into the host cell (CHO-DXB11) was performed using LONZA's NUCLEOFECTOR® 2b (NUCLEOFECTOR® is a registered trademark of Lonza Cologne GmbH). The landing pad plasmid used for transfection was linearized with the restriction enzymes EcoRV and SalI. Four hours after the transfection, the medium was replaced with a hypoxanthine/thymidine-free medium, and the shake culture of cells was initiated. Approximately two weeks later, single cell sorting was performed using Sony's cell sorter SH800. At the time of sorting, the cell population within the top 2% having a high GFP fluorescence intensity was sorted. A 488 nm semiconductor laser was used to excite GFP. Single cell sorted cells were expanded and cultured, and genomic DNA was extracted from each cell clone. Using the recovered genomic DNA, the number of copies of the GFP gene introduced into each cell clone was measured using Bio-Rad's QX200™ DROPLET DIGITAL® PCR system (DROPLET DIGITAL® is a registered trademark of Bio-Rad Laboratories, Inc.). The copy number of the GFP gene was used as the copy number of the landing pad possessed by the cell, and cell clones into which one or two copies of the landing pad were introduced were selected. Each of the obtained cell clones was used as a TI host cell candidate in subsequent experiments.

Example 4

Figure 3:
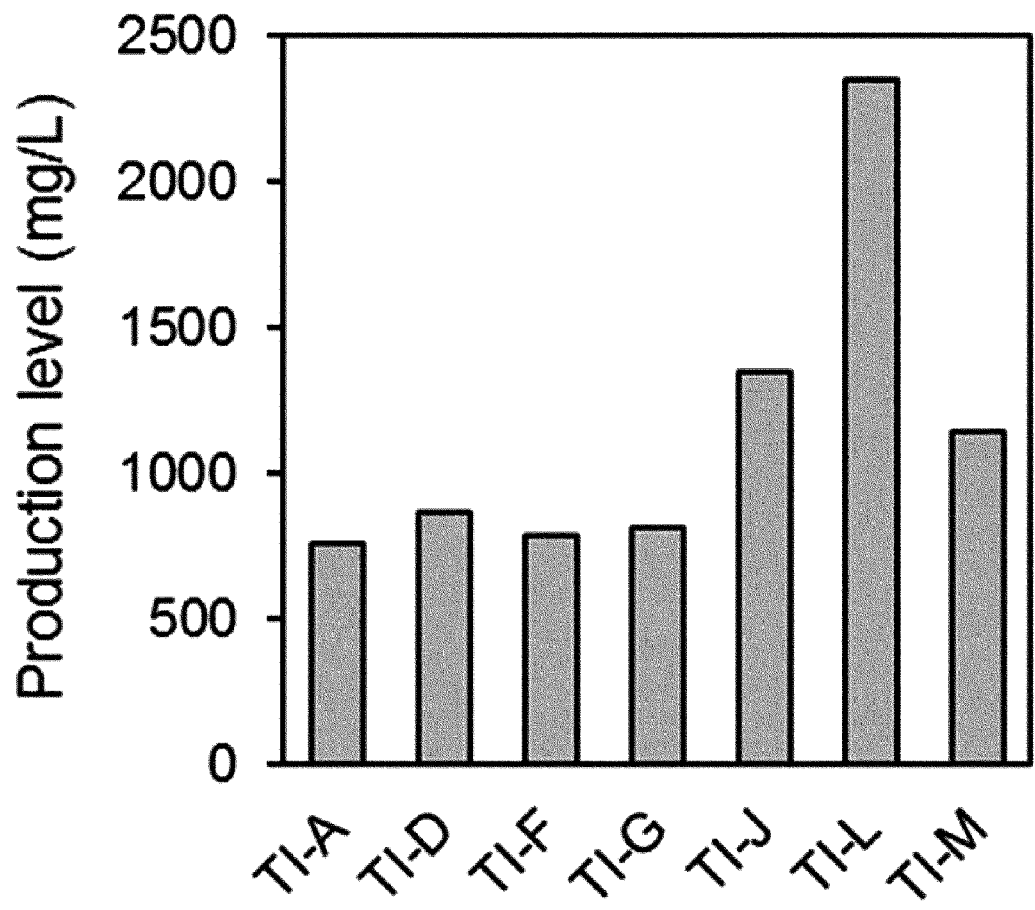
FIG. 3 shows the results of a two-week production culture of antibody-expressing cell clones established after TI. The horizontal axis shows the names of the established antibody-producing cell clones, and the vertical axis shows the antibody production level per liter of culture solution (mg/L).

Introduction and Evaluation of an Antibody Gene into TI Host Cells by the Cassette Exchange Reaction An antibody gene was introduced and evaluated using the TI host cell candidates established in Example 3. A recombination plasmid carrying the mAb-A antibody gene (one copy each of the H chain and L chain) and a Cre expression plasmid were co-introduced into each TI host cell using NUCLEOFECTOR® 2b, and the cassette exchange reaction was carried out. The cassette exchange reaction replaces the DNA cassette introduced into the TI host cell genome with the DNA cassette comprising the mAb-A antibody gene. The medium was exchanged four hours after transfection, and about two weeks later, cells having no GFP fluorescence were fractionated to establish antibody-expressing cells derived from each TI host. At this time, it was not possible to obtain viable cells from some TI host cells after the cassette exchange reaction. The established antibody-expressing cell clones were used in two weeks of production culture, and the antibody-producing ability was evaluated. As a result, antibody-expressing cell clones derived from three TI hosts (TI-J, L, and M) showed an antibody production amount of 1000 mg/L or more on the 14th day of production culture (FIG. 3).

Example 5

Figure 4:
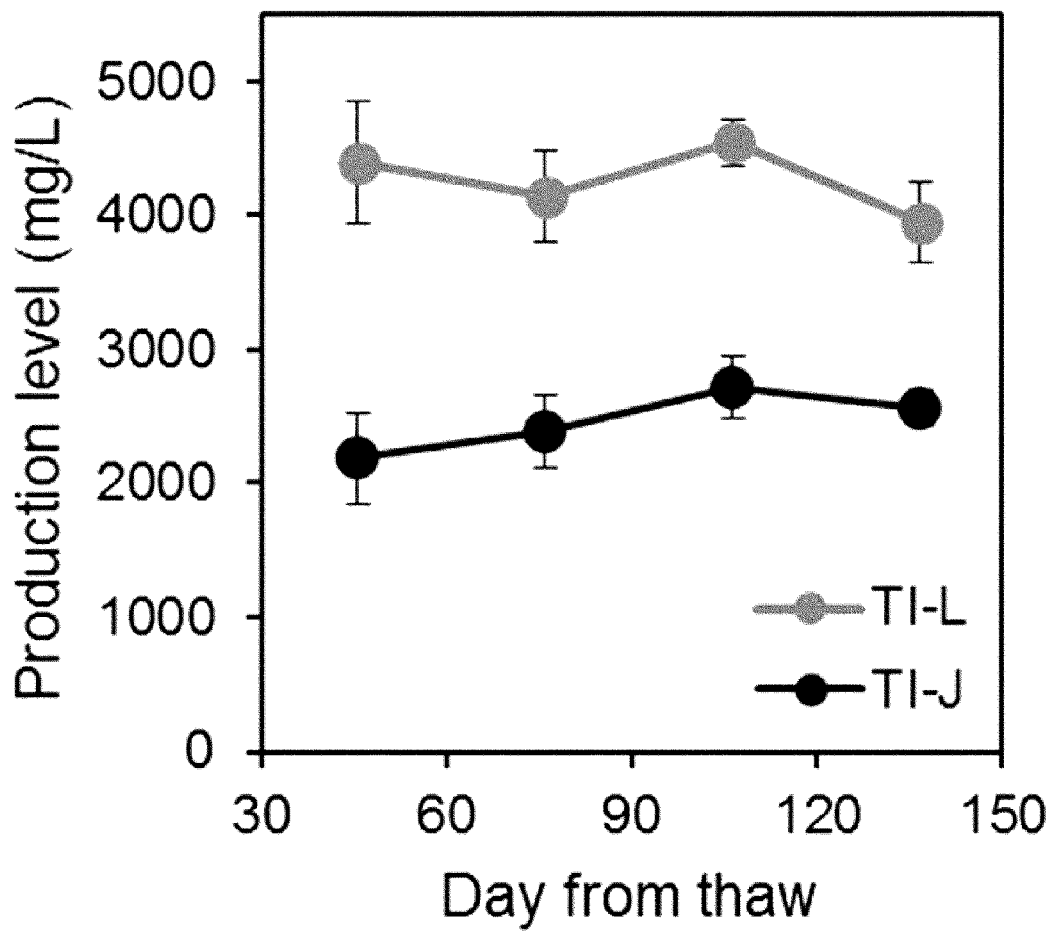
FIG. 4 shows changes in antibody production over time after freeze-thawing of antibody-producing cell clones TI-L and TI-J. The horizontal axis shows the time (days) after thawing cryopreserved cells, and the vertical axis shows the antibody production level per liter of culture solution (mg/L).

Evaluation of Long-Term Stability of the Production Ability of Antibody-Expressing Cells Derived from TI Hosts A recombination plasmid carrying the mAb-A antibody gene (2 copies each of the H chain and L chain) was newly prepared, and a cassette exchange reaction was carried out similarly as in Example 4 on two TI host cells (TI-J and L). The obtained antibody-expressing cell clones were cryopreserved and subjected to long-term passage culture for about 140 days after thawing. During this period, production cultures were performed at intervals of about 30 days to evaluate changes in antibody-producing ability after cell thawing. As a result, each antibody-expressing clone derived from TI-J and TI-L cells maintained high antibody-producing ability for a long period of 140 days, and the mean values for 140 days were about 2400 and 4200 mg/L, respectively (FIG. 4).

Example 6

Figure 5:
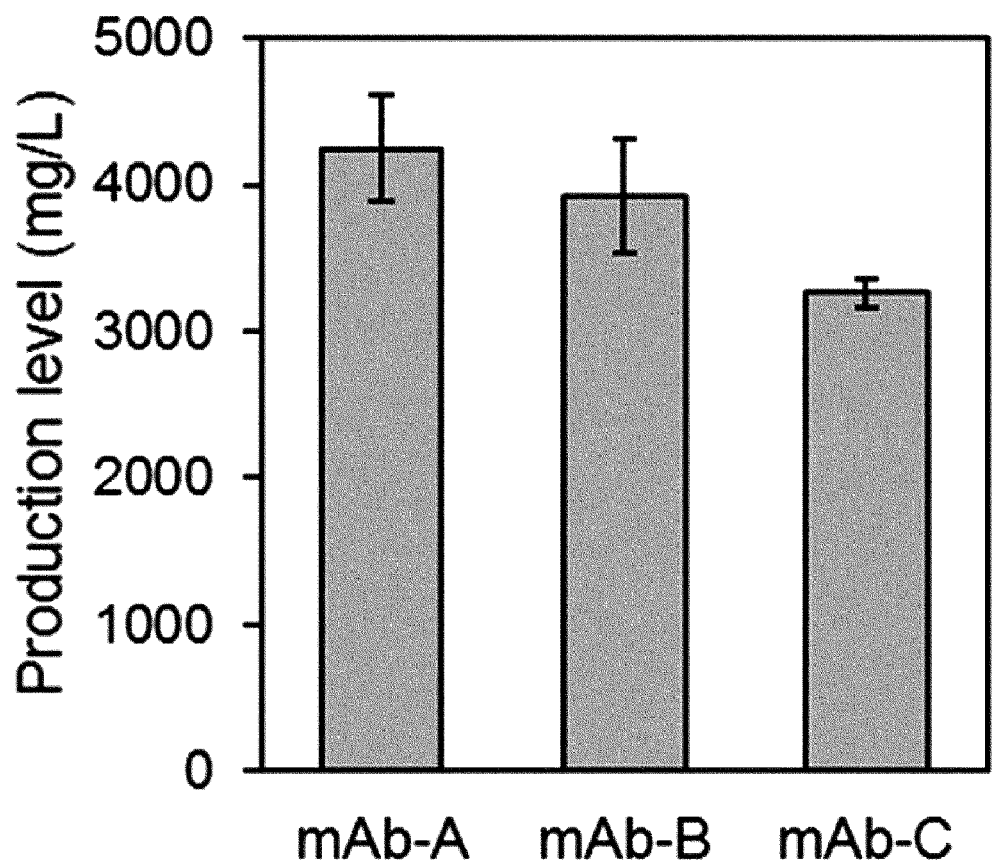
FIG. 5 shows the antibody production level by other antibody-producing cell clones prepared by incorporating the genes of different antibodies into the recombination plasmid of FIG. 2. The horizontal axis shows the names of the produced antibodies, and the vertical axis shows the antibody production level per liter of culture solution (mg/L).

Evaluation of the Production Ability of TI Host Cells Using Different Antibody Genes Recombination plasmids carrying each of the three antibody genes mAb-A, B, and C (two copies each of the H chain and L chain) were newly prepared, and a cassette exchange reaction was carried out similarly as in Example 4 on TI-L cells, which is the parent cell of the cell clone that had the highest antibody-producing ability in the production culture. Then, cells having no GFP fluorescence were fractionated, and three antibody-expressing cells derived from the TI host were established. As a result of two weeks of production culture, the antibody-expressing cells derived from TI-L cells also had a high antibody-producing ability for the three different antibodies mAb-A, B, and C (FIG. 5).

Example 7

Identification of the Landing Pad Integration Site

Figure 6:
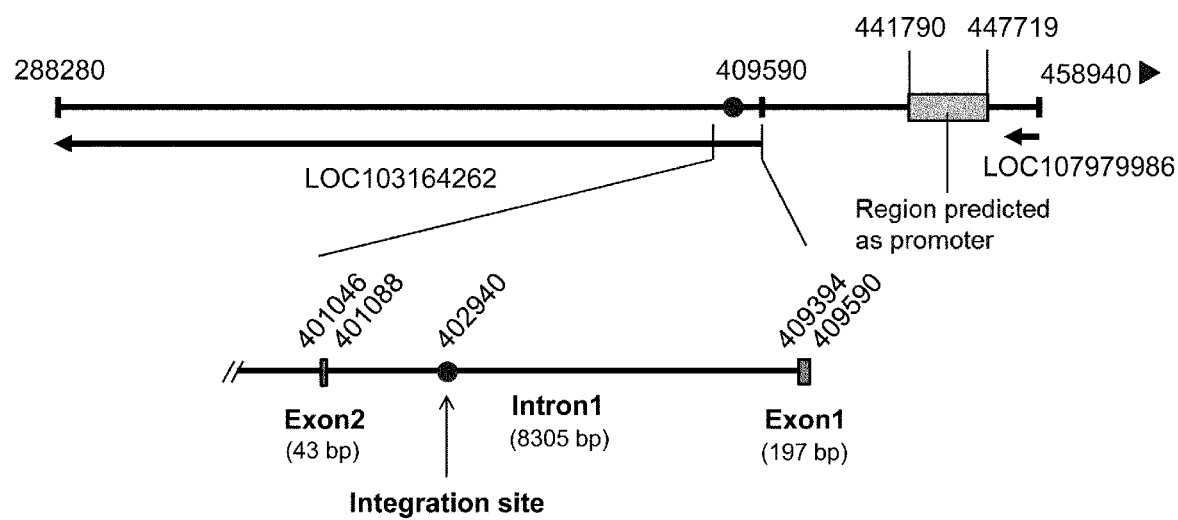
FIG. 6 shows schematically the position of introduction of the landing pad on the genome of the parent cell TI-L (the transformed cell before substitution of the landing pad with the exchange cassette) of the antibody-producing cell clone having the highest antibody production level. In the figure, the part indicated by "Integration site" is the integration site of the landing pad identified in the present disclosure. The integration site is 6651 bp downstream from the (5'end) of the CCDC91 gene and 6454 bp downstream from the upstream (5'end) of Intron 1. The 5 kb nucleotide sequence upstream (5' side in the genomic sequence) and the 5 kb nucleotide sequence downstream (3' side in the genomic sequence) of the "Integration site" are shown in SEQ ID NOs: 1 and 2, respectively.

Genomic DNA was extracted from TI-L cells, which are the parent cells of the cell clone that had the highest antibody-producing ability in production culture. Whole-genome sequencing of TI host cells was performed using two next-generation sequencers, the PACBIO® SEQUEL™ system by Pacific Biosciences and the HISEQ® sequencing system by ILLUMINA®. First, eight long reads having the landing pad DNA sequence were extracted from all read data obtained from the PACBIO® SEQUEL™ system, and these were subjected to a Blast search against the CHO cell genomic sequence (CHO-K1 [ATCC] _RefSeq_2014) on the public Nucleotide Database. From the search results, the genomic region with the highest homology was identified as the integration site for the landing pad plasmid, and the theoretical genomic structure of the integration site containing the landing pad was designed. As a result of mapping all the read data obtained from the HISEQ® sequencing system to the designed theoretical genomic structure, it was confirmed to be mapped to the designed genomic structure just as theorized. As a result of identification, the landing pad was inserted in the first intron (SEQ ID NO: 3) of the CCDC91 (coiled-coil domain-containing protein 91) gene (Gene symbol: LOC103164262) on NW_003614838.1 registered in CHOK1 RefSeq scaffold (as of January 2019) (FIG. 6). The CCDC91 gene is mapped on the antisense sequence of NW_003614838.1. Therefore, the nucleotide sequence of SEQ ID NO: 3 is also mapped on the antisense sequence of NW_003614838.1. In addition, about 32 kbp upstream of the CCDC91 gene, there was a region highly homologous to the promoter of the CCDC91 gene in the mouse genomic sequence (GRCm38.p6). The 5 kb nucleotide sequences located on the 5'side and 3'side of the genomic sequence centering on the identified integration site are as shown in SEQ ID NOS: 1 and 2, respectively. Therefore, the positional relationship between each nucleotide sequence and the landing pad is as follows:

5'-(SEQ ID NO: 1)-[landing pad]-(SEQ ID NO: 2)-3'

INDUSTRIAL APPLICABILITY

The hotspot provided by the present disclosure is useful for the production by TI of transformed cells for making animal cells produce exogenous DNA. For example, when a DNA encoding an antibody is introduced into the hotspot of the present disclosure, transformed cells useful for antibody production can be obtained with high probability.

---

The invention claimed is:

1. A method for integrating an exogenous DNA encoding a polypeptide of interest into the genome of a Chinese hamster ovary (CHO) cell, wherein the method comprises integrating the exogenous DNA into the first intron of the coiled-coil domain-containing protein 91 (CCDC91) gene of the genome of the CHO cell, wherein the nucleotide sequence of the first intron is SEQ ID NO: 3.

2. A method for producing a polypeptide of interest, wherein the method comprises the steps of:
   (1) integrating an exogenous DNA encoding the polypeptide of interest into the first intron of the coiled-coil domain-containing protein 91 (CCDC91) gene of the genome of a CHO cell, wherein the nucleotide sequence of the first intron is SEQ ID NO: 3;
   (2) culturing the CHO cell into which the exogenous DNA has been integrated to produce the polypeptide of interest; and
   (3) recovering the polypeptide of interest.

3. The method according to claim 2, wherein the step of integrating the exogenous DNA encoding the polypeptide of interest includes the following steps (i)-(ii):
   (i) introducing into the CHO cell a DNA cassette for integrating the exogenous DNA by an exchange reaction; and
   (ii) integrating the exogenous DNA into the first intron site by a recombinase which recognizes the DNA cassette of (i) as a target site.

4. The method according to claim 1, wherein the polypeptide of interest is an antigen-binding molecule.

5. The method according to claim 4, wherein the antigen-binding molecule is an antibody.

6. An isolated Chinese hamster ovary (CHO) cell comprising an exogenous DNA encoding a polypeptide of interest integrated into the first intron of the coiled-coil domain-containing protein 91 (CCDC91) gene of the genome of the CHO cell, wherein the nucleotide sequence of the first intron is SEQ ID NO: 3.

7. The CHO cell according to claim 6, wherein the polypeptide of interest is an antigen-binding molecule.

8. The CHO cell according to claim 7, wherein the antigen-binding molecule is an antibody.

9. The method according to claim 2, wherein the polypeptide of interest is an antigen-binding molecule.

10. The method according to claim 9, wherein the antigen-binding molecule is an antibody.

11. The method according to claim 1, wherein the CHO cell into which the exogenous DNA has been integrated overexpresses the polypeptide of interest.

12. The CHO cell according to claim 6, wherein the CHO cell overexpresses the polypeptide of interest.

* * * * *